United States Patent [19]
Gauthier et al.

[11] Patent Number: 6,017,318
[45] Date of Patent: Jan. 25, 2000

[54] FEEDBACK CONTROLLED DRUG DELIVERY SYSTEM

[75] Inventors: Robert T. Gauthier, San Diego; Steve M. Harrington, Cardiff; John Bridwell, San Diego; Ronald Irwin, Fortuna; Richard A. Sorich, Encinitas, all of Calif.

[73] Assignee: Gensia Automedics, Inc., San Diego, Calif.

[21] Appl. No.: 08/990,846

[22] Filed: Dec. 15, 1997

Related U.S. Application Data

[63] Continuation-in-part of application No. 08/474,456, Jun. 7, 1995, abandoned, which is a continuation-in-part of application No. 08/386,916, Feb. 7, 1995, Pat. No. 5,697,899.

[51] Int. Cl.[7] .................................................. A61B 5/00
[52] U.S. Cl. ............................ 600/578; 604/43; 604/258
[58] Field of Search .................................. 600/573, 578, 600/579, 581, 584; 604/27–30, 32, 43, 52, 53, 181, 183, 257, 258, 262

[56] References Cited

U.S. PATENT DOCUMENTS

| | | | |
|---|---|---|---|
| 4,054,415 | 10/1977 | Seligson et al. | 23/253 R |
| 4,280,494 | 7/1981 | Cosgrove, Jr. et al. | 128/213 R |
| 4,532,936 | 8/1985 | LeVeen et al. | |
| 4,846,787 | 7/1989 | Aall-Flood et al. | |
| 4,888,004 | 12/1989 | Williamson et al. | |
| 5,069,661 | 12/1991 | Trudell. | |
| 5,134,079 | 7/1992 | Cusack et al. | 436/53 |
| 5,273,517 | 12/1993 | Barone et al. | 494/37 |
| 5,325,867 | 7/1994 | Skrabal et al. | |

OTHER PUBLICATIONS

Carr et al., "Glycoprotein IIb/IIIa Blockade Inhibits Platelet--Mediated Force Development and Reduces Gel Elastic Modulus," *Thrombosis and Haemostasis*, 73(3):499–505 (1995).

Frucht et al., "Computer–Assited Blood Pressure Control By Cardiovascular Drugs–Problems in Developing a Closed Loop Control System," *Anasth. Intensivther. Notfallmed.* 21:333–337 (1986).

Jannett, T.C. et al., "Simulation of Adaptive Control of Anticoagulation During Hemodialysis," *Biomedical Application of Automatic Control, Proceedings from the Annual International Conference of the IEEE Engineering in Medicine and Biology Society*, 13:2147–2148 (1991).

Kershaw et al., "Computer–Assisted Dosing of Heparin: Management with a Pharmacy–Based Anticoagulation Service," *Archives of Internal Medicine*, 154:1005–1001 (1994).

Mungall, Dennis, et al., "A Prospective Randomized Comparison of the Accuracy of Computer–Assisted Versus GUSTO Nomogram–Directed Heparin Therapy," *Clinical Pharmacology & Therapeutics*, 55(5):591–596 (1994).

*Primary Examiner*—Max Hindenburg
*Attorney, Agent, or Firm*—Lyon & Lyon LLP

[57] ABSTRACT

A feedback controlled drug delivery system includes the automated sampling and analysis of a patient sample and dosing the patient based on the analysis. Automated sampling may be performed by direct analysis of the patient sample, such as for the measurement of a blood sample coagulation state or a glucose level. The drug delivery system includes a sample set that has a bidirectional patient tube that allows for delivery of the patient sample to an analyzer, and at another time, the infusion of a therapeutic drug. A controller receives a measurement from the analyzer, and based on that measurement, adjusts the delivery of the therapeutic fluid. The sample set has a quick—clear Leur fitting that allows for more effectively clearing a first fluid from a Leur fitting when starting a second fluid. The system also has a reagent cassette holder that protects, using a foam gasket, a reagent on a sample slide. Further, the system provides an interlock apparatus that assures a sample tube is occluded by either or both a slide clamp and by a platen arm compressing the sample tube to a peristaltic pump.

29 Claims, 16 Drawing Sheets

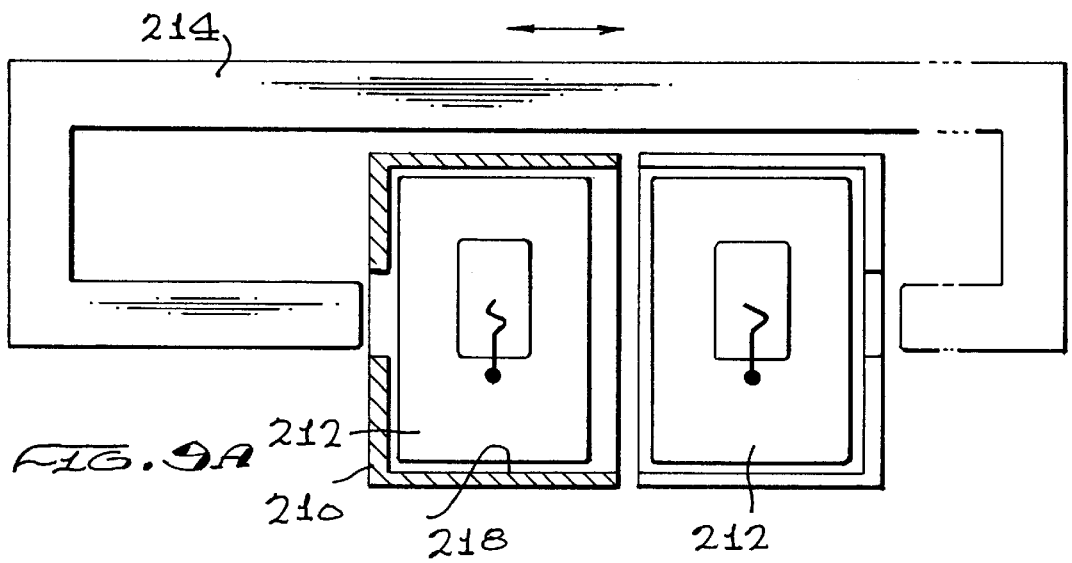
FIG. 9A
FIG. 9B
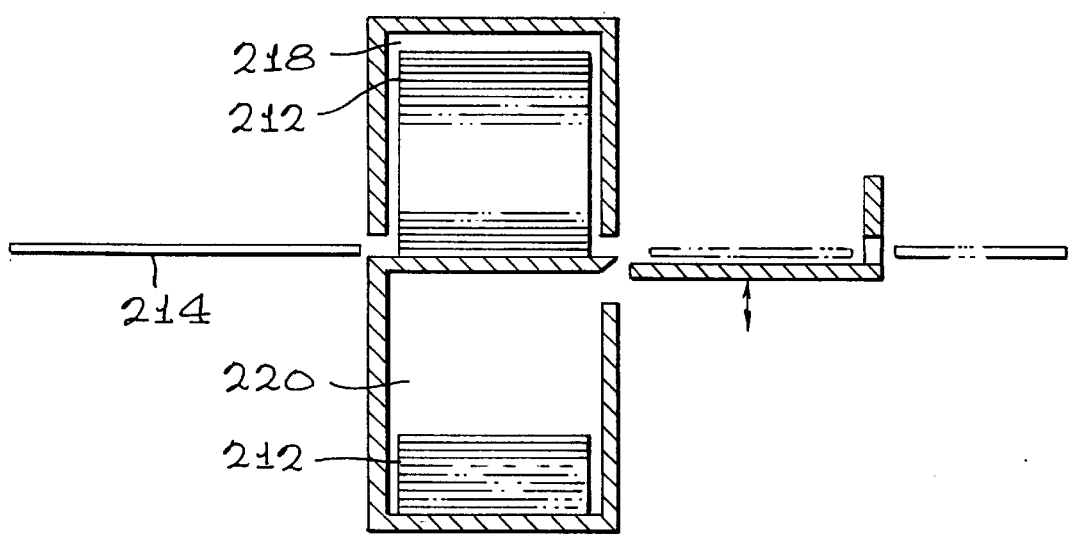
FIG. 10
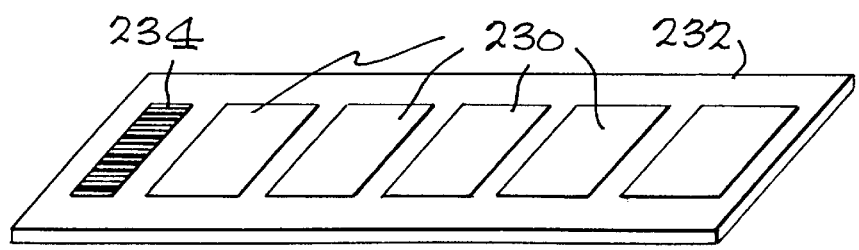

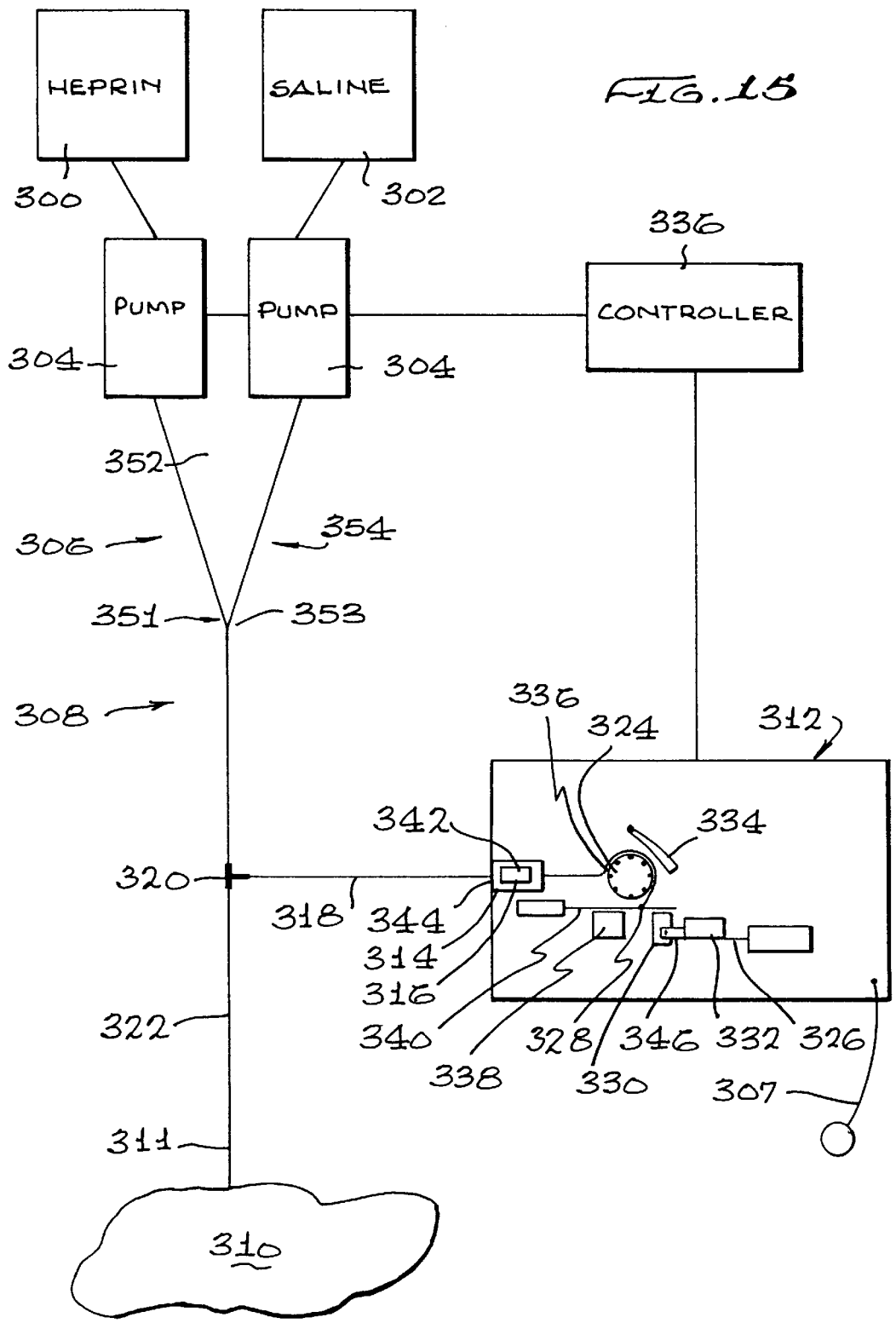

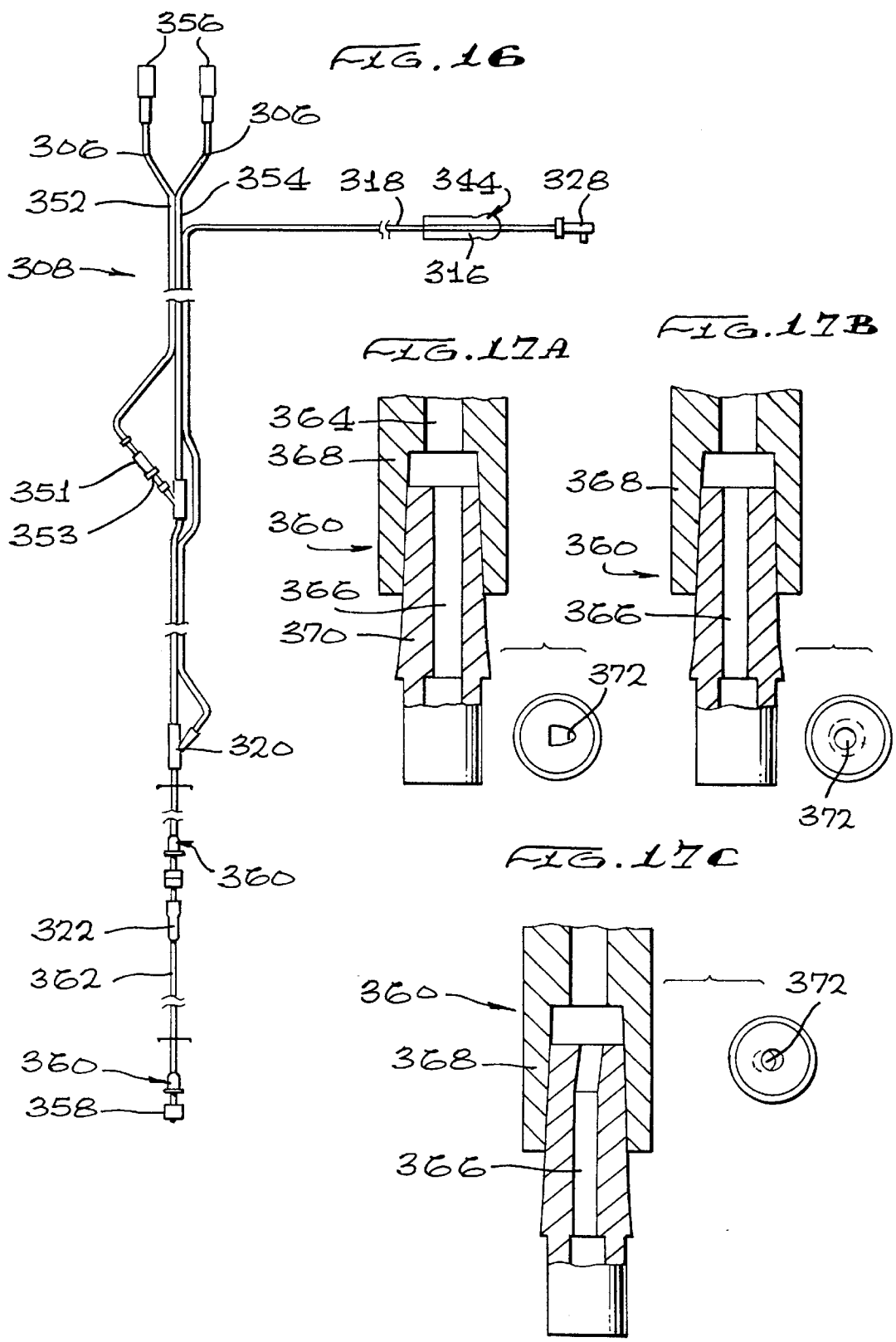

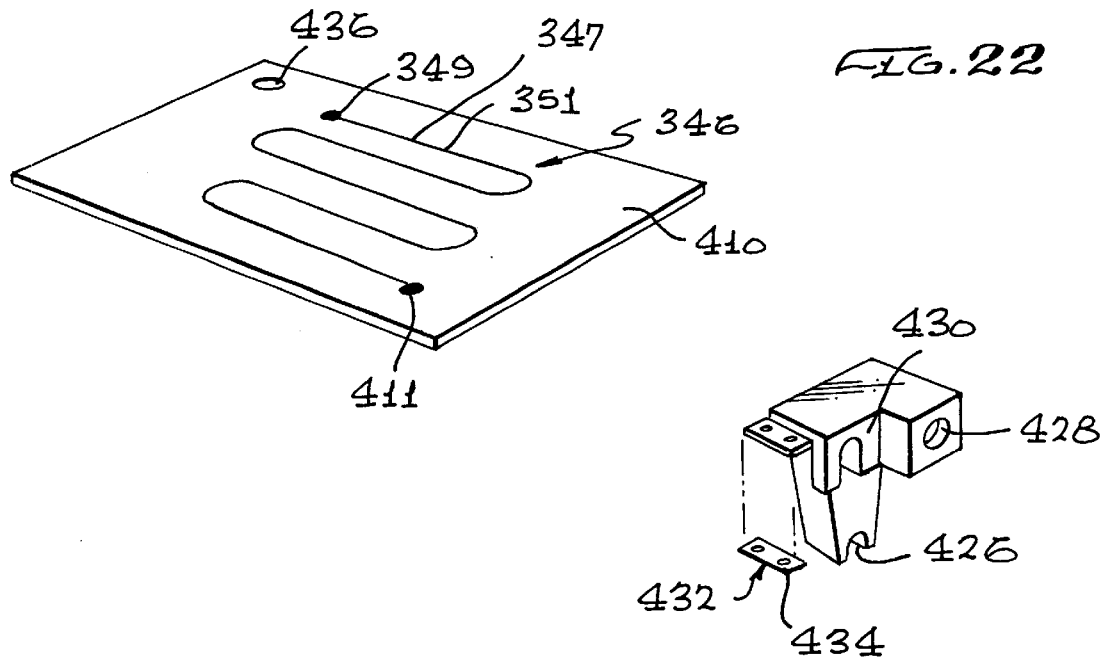
FIG. 22
FIG. 24
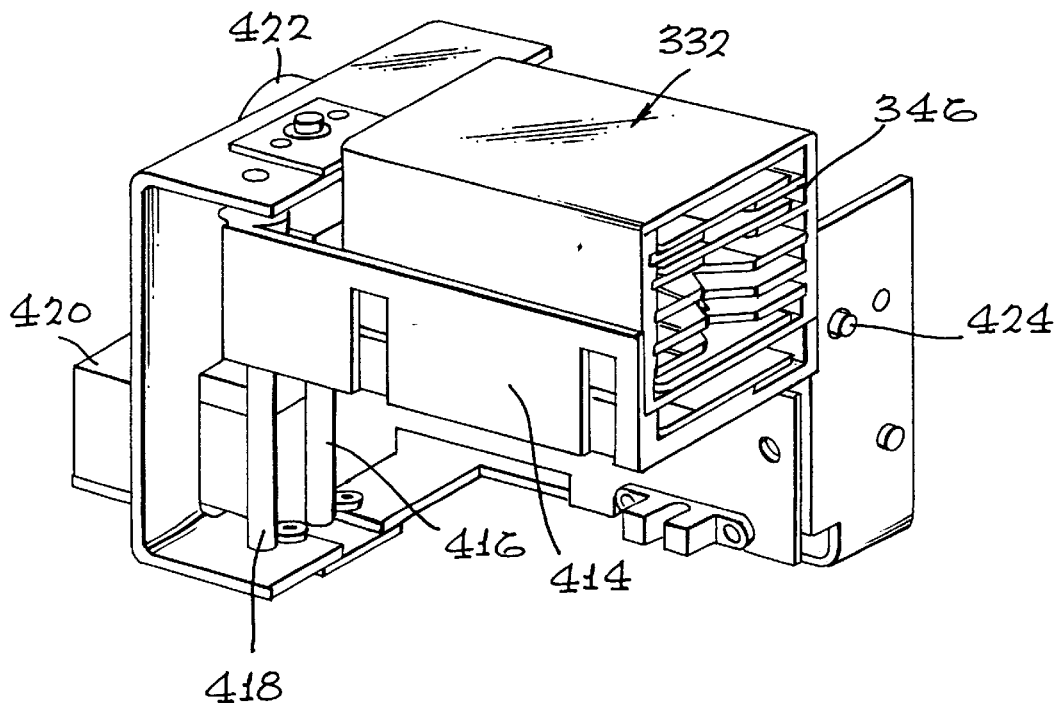
FIG. 23

FEEDBACK CONTROLLED DRUG DELIVERY SYSTEM

RELATED APPLICATION INFORMATION

This application is a continuation-in-part application of Ser. No. 08/474,456 filed Jun. 7, 1995, now abandoned which is a continuation-in-part application of Ser. No. 08/386,916, filed Feb. 7, 1995, U.S. Pat. No. 5,697,899, both entitled "Feedback Controlled Drug Delivery System". The above referenced documents are herein incorporated by reference.

FIELD OF THE INVENTION

This invention relates to the field of feedback controlled drug delivery system. In other aspects, this invention relates to systems for the automatic sampling of the patient sample or state. More particularly, this invention relates to the field of automatic monitoring systems used in conjunction with variable dose drug delivery systems, especially those for use with drug administration which otherwise requires a high degree of monitoring by health care professionals.

BACKGROUND OF THE INVENTION

A wide variety of drug delivery systems are known to the art, ranging from systems totally relying upon the healthcare professional for dosing decisions and administration to highly automated systems performing one or more tasks such as monitoring, analyzing, dosing decisions and dosing.

At the nonautomated, simplest end of the spectrum, a drug delivery system may comprise a preset regimen performed at a preset infusion rate without feedback, such as when a patient is given a prescribed dosing regimen. At a higher level of control, feedback systems are utilized in which analysis of the patient's current condition is utilized in a feedback controlled manner as input for the dosing analysis. These steps may be performed by the healthcare professional with or without the use of automation or computational tools.

Example of a nomogram based, nonautomated drug delivery system includes various heparin delivery systems now in wide spread use. Other such systems use hirudin, hirulog and other direct thrombin inhibitors. See, e.g., Carr et al., "Glycoprotein IIb/IIIa Blockade Inhibits Platelet-Mediated Force Development and Reduces Gel Elastic Modulus", Thrombosis and Haemostasis, pp 499–505. Heparin is a well known anticoagulant used to avoid clotting, such as during dialysis, thrombolytic therapy, acute unstable angina, cardiac catheterization, coronary artery bypass surgery, stent placement and PTCA, pulmonary embolism, deep vein thrombosis, treatment of transcient ischemic attack and stroke. At certain intervals, blood is drawn from the patient, and analyzed for its coagulation ability. Although heparin is generally viewed as a relative safe and efficacious drug, it may result in an increased risk of hemorrhage, and has proved difficult to select ideal heparin dosage. There is a wide variation in patient-to-patient response, both in the heparin concentration which results from a given heparin infusion rate, and in the patient response to a given heparin concentration. Nonautomated control is difficult and often imprecise.

Various commercially available analysis units are available to analyze a small amount, e.g., a drop, of patient blood to determine the coagulation state of the blood. Based upon this analysis, dosing decisions are made ad hoc or with the aid of a nomogram. The heparin is then administered to the patient based on this decision.

Various proposals have been made to automate the dosing decision step in the heparin delivery. In Dennis R. Mungall, et al., "A Prospective Randomized Comparison of the Accuracy of Computer-Assisted Versus GUSTO Nomogram-directed heparin Therapy", Clinical Pharmacology & Therapeutics, May, 1994, pp 591–596, a computer system utilized the activated partial thromboplastin time (APTT) measured on a preset interval as input to determine dosing decisions. A Bayesian forecasting computer program was utilized, assuming a non-linear pharmacokinetic model for heparin. Initial estimates of heparin requirements were based on prior knowledge of demographic characteristics, specifically weight, sex, and current smoking condition. Similarly, in Kershaw et al., "Computer-Assisted Dosing of heparin, Management With a Pharmacy-Based Anticoagulation Service", Archives of Internal Medicine, May 9, 1994, pp 1005–1011, a computer-assisted dosing of heparin was performed. APTT measurements were used as the input to the system. Finally, specific work has occurred in an attempt to optimize drug delivery where sparse measurements are available. See, e.g., T.C. Jannett et al., "Simulation of Adaptive Control of Anticoagulation During Hemodialysis", Biomedical Applications of Automatic Control, Proceedings from the Annual International Conference of the IEEE Engineering in Medicine and Biology Society, Vol. 13, No. 5, 1991, pp 2147–2148.

Various adaptive control systems have been proposed. These systems attempt to utilize data obtained historically and from individual patient response as input to the control system determining drug dosing. These adaptive control systems have particular applicability to delivery systems in which sparse measurements are available. One proposed system by Jannett et al., above, utilizes a model based system with parameter estimation. Sparse measurements, at infrequent or differently timed intervals, are utilized in an attempt to estimate appropriate drug delivery.

At a higher level of integration, various automated drug delivery systems are known to the art. Relatively simple systems utilizing noninvasive monitoring systems monitor a patient variable and provide dosing based upon decisions made by a control system in a feedback controlled manner. For example, automated blood pressure monitoring systems exist. Automated blood pressure measurement devices are automatically activated, typically at preset time intervals, which cause the increase in cuff pressure on an automated blood pressure measurement system, and then the detection of the patient's blood pressure. These systems generally attempt to hold the patient at a preset level, such as a desired blood pressure level, See, e.g., Cosgrove Jr., et al. U.S. Pat. No. 4,280,494, or at a higher level of complexity attempt to mimic the natural variations in a patient's physiologic variable, such as a circadian rhythm in blood pressure. See, e.g., Frucht et al., "Computer-Assisted Blood Pressure Control By Cardiovascular Drugs - Problems in Developing a Closed Loop Control System", Anasth. Intensivther. Notfallmed. 21 (1986).

Yet another noninvasive, feedback controlled system is the GenESA system of Gensia, Inc. which monitors a patient's heart rate as a control input for a system which causes delivery of a exercise simulating agent, such as arbutamine, so as to mimic the effects of aerobic exercise. In one application, such system may be utilized to perform a cardiac stress test on patients, such as by varying the cardiac stress as a function of time. The control of certain physiologic parameters requires the invasive monitoring of the patient, such as in systems requiring direct analysis of the patient's blood. A system from VIA Medical automatically draws and analyzes patient blood. A delivery set is connected to the patient's vein which is utilized for the dual function of fluid delivery, such as a physiologic solution, and blood withdrawal from the patient. A pump is used to draw the blood from the patient through the delivery set. Analysis occurs by drawing the blood through a closed circuit which contains a sensor in-line. Sensors external to the patient measure various analytes in the blood. In suggested operation, the blood drawn from the patient is reinfused to the patient.

Yet another blood analysis system is that shown in Cusack U.S. Pat. No. 5,134,079. A fluid sample collection system utilizes a patient sample, such as blood, with an immiscible fluid, such as air, and a washing fluid, such as saline, to segment portions of the patient sample and to transport them to an analyzer. The blood and saline are connected by a fluid path, which in combination forms a transfer tube to pass the blood and saline alternately to the analyzer. From a fluidics standpoint, the patient sample and the immiscible fluid are input from separate input ports which form a Y-connection with the fluid path towards the analyzer. A third input port forms a T-connection with the fluid path and provides input for the immiscible fluid to the fluid path. A downstream pump causes motion through the fluid path tube. A detector is positioned downstream of the pump but upstream of the output port to the analyzer. In each of the modes of operation described, segmentation of the blood is required. No provision is made for return of the sampled blood to the patient which is not used in the analysis.

Various blood gas measuring systems are known in the art, some of which are noninvasive and some of which are invasive. One such system is made by FOxS Systems which comprises an inter-arterial blood gas system which measures pH, $PCO_2$, $PO_2$, and temperature on a continuous basis. The system uses optical fluorescent sensors optimized for each analyte of interest. A system by Diametrics performs blood gas analysis utilizing a small cartridge inserted into the front of an IRMA analyzer. After a calibration step, arterial blood is injected into the cartridge which performs the analysis.

The Biostator™ system of Miles Laboratories is an automated, invasive feedback controlled drug delivery system. One line connects the patient in a closed circuit serving to provide fluid delivery, such as saline, to the patient as well as to sample blood from the patient. The sampled blood is then analyzed to determine the glucose concentration, which is used to calculate an insulin infusion rate to control the blood glucose level.

While much progress has been made in the general field of automated, feedback controlled drug delivery, deficiencies remain for certain applications. Current systems for therapeutic dosing are often time consuming, requiring the direct input of a healthcare professional. Automatic analysis is often difficult or impossible and requires substantial skill and training on the part of the healthcare professional. Under such circumstances, it is difficult to perform such therapeutic dosing in a non-hospital environment, such as for in-home healthcare. Further, given the multiple steps and complex nature of the measurement, analysis and dosing steps, errors can occur in any one of these steps and cause a cumulative effect, causing risk for the patient. Further, a high degree of control is often required, especially for administration of anticoagulants, where the therapy has a narrow therapeutic index (i.e., too low a dose will result in decreased efficacy such as reoccurrence of deep vein thrombosis (DVT) and too high a dose will result in side effects (such as bleeding and hemorrhagic stroke). Current practice requires a multiple step operation, with each step incurring the potential for error. Generally, these steps are as follows: the patient is hooked to the heparin IV unit, a bolus of heparin is administered, a sample is drawn and sent to the lab, the lab analyzes the sample for APTT value, the nurse receives the results, with a possible delay of upwards of 1 hour, the heparin dose is determined based on the physician's order or by using a nomogram, the IV pump is adjusted with the new heparin rate and the next sample time is determined. Cumulative errors can result in suboptimal delivery rates.

Despite the numerous attempts to provide a more automated and reliable system for drug delivery, no satisfactory solution has been proposed for systems requiring invasive monitoring of patient blood and subsequent control of anticoagulant effects.

For the delivery of heparin, the rationale for feedback-controlled delivery is based on the following observations:

(1) individual heparin response is variable (a four-fold range in sensitivity and a three-fold range in the rate at which heparin is metabolized/eliminated is not uncommon);

(2) the non-linear dose response curve of individual patients requires frequent titration;

(3) tight control of APTT requires frequent infusion adjustments;

(4) heparin is frequently under-dosed resulting in sub-therapeutic anticoagulation;

(5) over-dosing resulting in excessive bleeding, which can be avoided.

In the current practice of patient management for heparin titration, the following steps have be repeated: a blood sample must be taken and sent to the lab, the clinician must wait for results (with significant turnaround time), a nomogram must be used to calculate a new infusion rate, and the infusion rate on the pump must then be manually adjusted. The potential for error across these steps can be minimized and the effort required by nursing staff greatly reduced by the use of an automated system.

SUMMARY OF THE INVENTION

The invention comprises a feedback controlled drug delivery system particularly adapted for performing automated blood analysis, computing optimal dosage and controlling a drug delivery system to administer the dose to the patient. The sampling methods and apparatus, the control system and the drug delivery interconnect all include novel aspects of this invention. In the preferred embodiment, this invention is utilized with a feedback controlled drug delivery system requiring automated withdrawal and analysis of patient blood, such as for its coagulation state, and determination of the optimal dosage to be delivered. That optimal amount is calculated for a system having infrequent measurements, and then drug delivery, such as of an anticoagulant, is administered.

From a system standpoint, one or more sources of drug are provided to the patient in a controlled manner such as from delivery through a pump system. Control of the pumps is performed by a control system which utilizes the measured patient variable as input information.

Structurally, one or more drug sources and, optionally, a source of fluid, e.g., saline, are operatively connected to a pump or pumps to control the flow rates to the patient. A novel manifold interconnects the patient, the saline source and the analyzer. The manifold includes an input port adapted to receive a fluid, e.g., saline or drug, a patient port adapted to output fluid to the patient and to receive blood from the patient, a fluid pathway connecting the saline port and the patient port, and a sample line connected to the fluid pathway, the sample line having an input connected to the fluid pathway and an output directed towards the analyzer. A pump force path is connected to the fluid pathway at a point between the saline port and the sample line, and is adapted to provide a pumping force on the fluid pathway. Optionally, a detector position between the pump force port and the access to the analyzer serves to detect the interface between blood and a more transparent fluid, such as saline.

In one embodiment, an integrated assembly is provided including one or more of the following: an integrated peristaltic pump (also known as a peri-pump) with retractable rotors, valves and an integrated disposal unit. Preferably, the peristaltic pump includes rollers which are moveable towards and away from the tube of the peri-pump to reduce deformation of the tube and to permit easy sterilization. Such an integrated, preferably disposable, unit provides for ease of operation and integration.

In operation, the manifold may be operated so as to sample the patient blood from a portion of the slug or discrete volume of blood displaced from the leading edge of the slug. In the preferred mode of operation, the saline delivery to the patient occurs in normal operation through the fluid pathway of the manifold. To obtain a blood sample, the saline source is disconnected from the fluid pathway, such as by operation of a poppet valve, followed by activation of the pumping force, thereby causing the saline in the fluid pathway to be drawn towards the pump force. This fluid flow in turn causes the patient blood to be drawn from the patient through the patient port of the manifold and through the fluid pathway. Once the blood has been pulled through the fluid pathway to a position past the intersection of the path to the analyzer, such as preferably determined by the detector, the blood slug will present a nonleading edge at the opening of the access to the analyzer. Blood from the nonleading edge of the slug may then be delivered to the analyzer. In the preferred embodiment, the blood is pushed towards the analyzer through the analyzer pathway, preferably by closing a valve at the patient port, driving fluid, e.g., saline, into the input port of the manifold, the resultant action being that the nonleading edge of the blood slug is forced towards the analyzer. Alternatively, a pumping force may draw the blood towards the analyzer.

In another aspect of this invention, a computer controlled system utilizes discrete, often sparse, sample data as input to the control system. Optionally, the patient's dosing history and/or response may be utilized in the control system. Expert systems may be utilized, especially for drugs which are difficult to administer. The control system outputs dosing information to the drug delivery device.

Analysis systems previously requiring individual test cartridges for a single test are combined in a multiple unit arrangement. In one embodiment, a carousel comprising multiple individual test units permits rotational motion of the test units beneath a source delivery location. In another embodiment, multiple individual test units are bundled in a stack arrangement, the new units being used on or taken from the stack as needed. A push unit may insert the individual test unit into the system, with an optional mating keyway being provided to remove the test unit from the system after analysis.

In yet another aspect of this invention, an interlock system is utilized to cooperatively and positively couple and interlock a drug source, e.g., heparin, to an input to the remainder of the drug delivery system. Optionally, the interface includes a system disable, such that if an unauthorized drug source is attempted to be used with the system, the system is disabled. In this way, a defined source of heparin may be used to minimize heparin variability and patient variability.

In yet another aspect of this invention, the system may include an inflatable cuff attached to the patient which is inflated prior to the sampling of blood from the patient. Preferably, the inflatable cuff is automatically inflated under system control. Blood withdrawal from the patient is facilitated. In yet another aspect of this invention, the system may include a motion detector so as to disable or otherwise limit system analysis during motion of the system.

It is yet a further object of this invention to provide an improved apparatus and method for automatic sampling of blood for use in an extracorporial circuit and analyzer.

It is a object of this invention to provide an improved device for use in the acute and home care drug delivery field.

It is yet a further object of this invention to provide an automated titration of drug based upon an automated measurement of a patient parameter.

It is yet a further object of this invention to provide a system useful with antiplatelet aggregation assays.

It is yet a further object of this invention to provide an improved system for the optimized delivery of a drug to maximize therapeutic benefit.

In yet another aspect of this invention, a novel arrangement of test cartridges is utilized for the analyzer.

It is a further object of this invention to provide a disposable venous blood sampling set for delivering a therapeutic solution to a patient at an intravenous entry point and removing a patient fluid sample from the intravenous entry point for analysis wherein the sampling set has a bidirectional patient tube that alternately allows a fluid to flow into the patient and at other times allows a sample of blood to flow from the patient.

In yet another aspect of the present invention, an interlocking apparatus is provided to assure that a sample line is engaged and occluded by a roller pump before a slide clamp is opened on the sample tube. The interlock further provides that the slide clamp occludes the sample tube before the sample tube is disengaged from the roller pump. A platen arm is used to compress the sample tube to the roller pump during use.

In yet another aspect of the present invention, a quick-clear Leur fitting is provided that quickly clears a first fluid from a Leur fitting when a second fluid is pumped through the Leur fitting.

In another aspect of the present invention, a feedback controlled drug delivery device and method is provided wherein blood is automatically sampled from the patient and moved to an analyzer where the analyzer makes measurements related to the drug. The measurement information is used by a controller to adjust the rate of drug being delivered to the patient.

Accordingly, it is an object of this invention to provide an automated, feedback controlled drug delivery system capable of use with drugs which require a high degree of patient monitoring.

BRIEF DESCRIPTION OF THE DRAWINGS

FIG. 3 is a plan view of a switch useful to alternately deliver blood to the analyzer or to a second output.

FIG. 9A shows a slidetray arrangement in top view.

FIG. 9B shows a slidetray arrangement in side view.

FIG. 10 shows a perspective view of a line of test cartridges and bar code.

FIG. 15 shows a block diagram view of a preferred embodiment of the present invention.

FIG. 16 shows a disposable venous blood sampling set for delivering a therapeutic solution to a patient at a intravenous entry point and withdrawing a patient fluid for analysis.

FIG. 17A shows a non-circular quick-clear Leur fitting.

FIG. 17B shows a non-concentric quick-clear Leur fitting.

FIG. 17C shows an off-axis quick-clear Leur fitting.

FIG. 22 shows a slide having a reagent area and tab-engagement hole.

FIG. 23 shows a reagent cassette positioned within a vertical positioning mechanism.

FIG. 24 shows a horizontal screw nut.

DETAILED DESCRIPTION OF THE INVENTION

Figure 1:
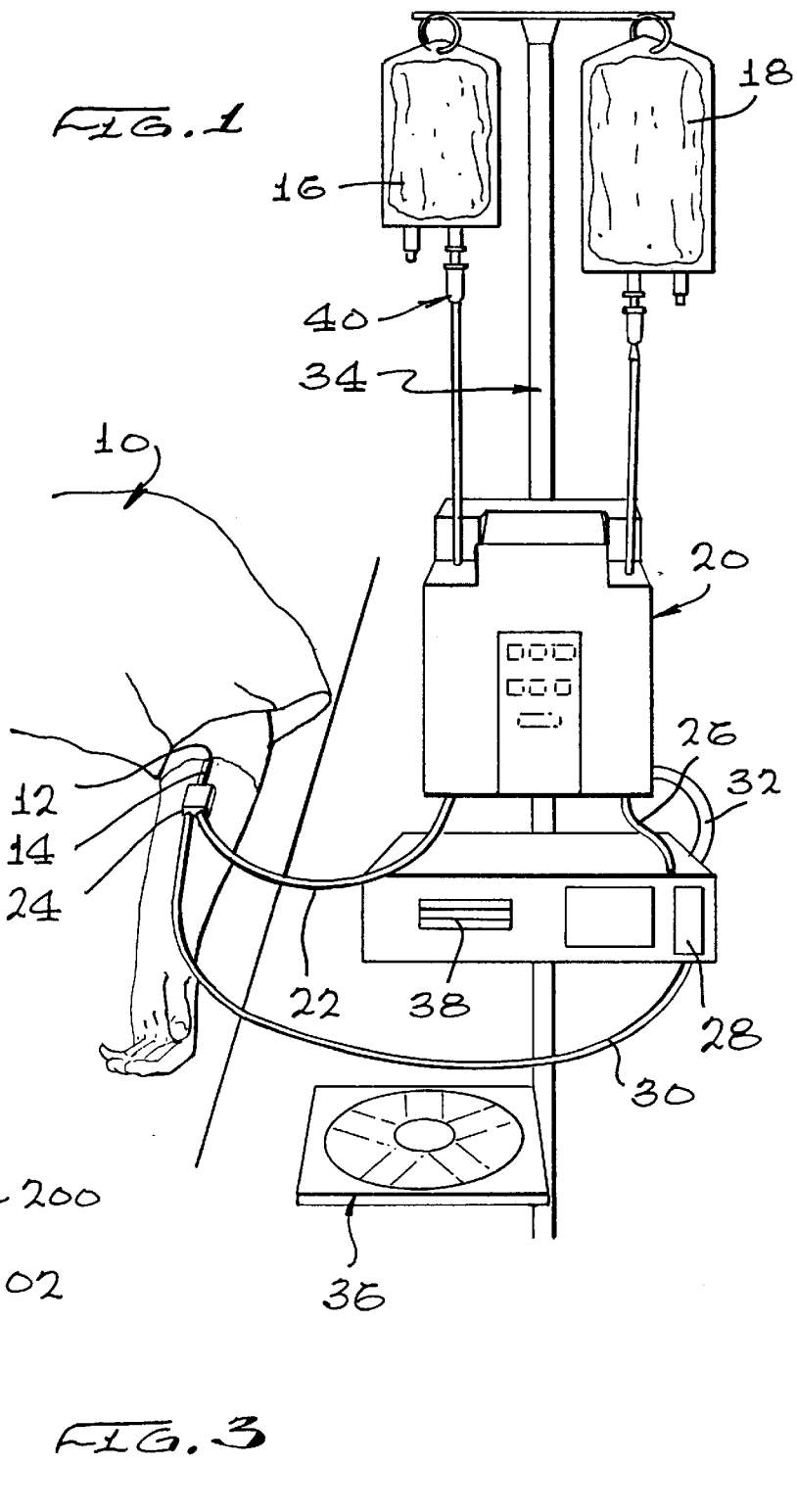
FIG. 1 shows a perspective view of the feedback controlled drug delivery system in one embodiment.

FIG. 1 shows a perspective view of the components of this invention in one preferred embodiment. A patient 10 is coupled to the system via a multiple lumen catheter (not shown) accessing a patient vein at access point 12. The preferred catheter is one manufactured by Arrow International, Inc. called the Arrow-Twin Cath®. One or more drug sources 16 and fluid source 18, such as saline, are connected to a pump system 20. The pump system preferably is capable of controlling fluid flow from the drug source 16 and the fluid source 18. The delivery of the drug to the patient 10 occurs through drug delivery tube 22 as measured and monitored by the pump 20. The delivery tube 22 is connected to one lumen of the multiple lumen catheter. The output of the fluid source 18 as measured and pumped by pump 20 is output via fluid delivery tube 26 to the analysis and control system 28. A tube 30 provides connection between the analysis and control system 28 and the patient 10, preferably through a different lumen of the multiple lumen catheter. The tube 30 preferably provides bidirection fluid flow, providing transfer from the fluid source 18 to the patient 10 of the fluid, e.g., saline, and at alternate times, transfer of the patient sample, such as blood from the patient 10 to the analysis and control system 28. The analysis and control system 28 provides control signals to the pump 20 via connection 32. The pump 20 and analysis and control system 28 may be conveniently disposed on a conventional rack 34.

The analysis and control system 28 is shown as a single integrated unit, though it may be formed into one or more components as desired. The analysis and control system 28 as shown is adapted to receive a multiple test unit 36 as inserted into a receiving slot 38. A directional arrow shows the action of insertion of the multiple test unit 36 into the receiving slot 38.

Figure 2:
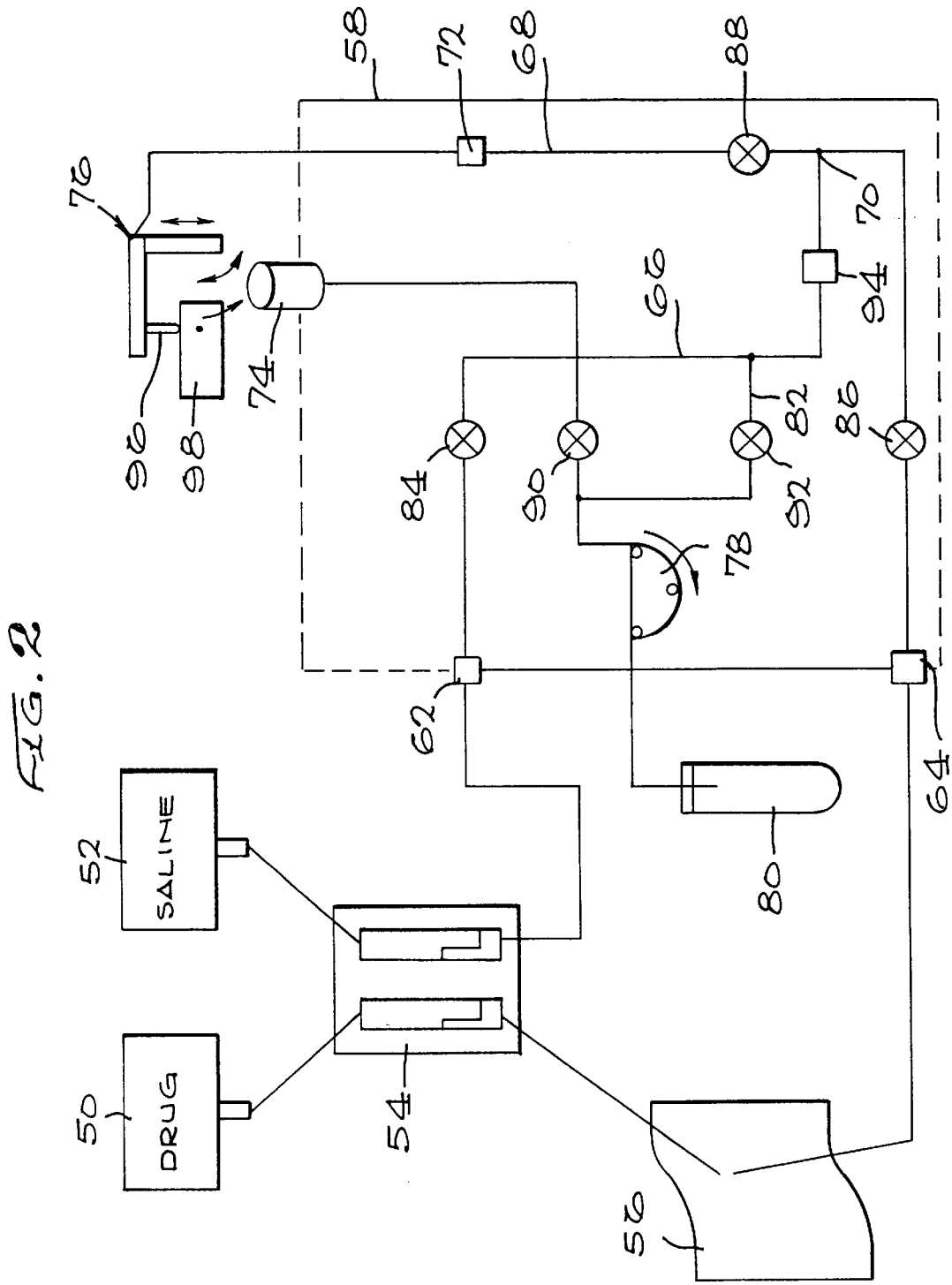
FIG. 2 shows a schematic diagram of the fluidic system in one embodiment.

In one aspect of this invention, an interlock system 40 is utilized to provide an interface between the drug source 16 and the pump 20. The interlock system 40 is adapted to provide limited interconnection between authorized drug sources 16 and the remainder of the system. The interlock system 40 may include mechanical interlock features and/or electrical interlock features. FIG. 2 shows a schematic version of one fluidic system in accordance with this invention. A drug source 50 and fluid source 52 are connected via fluid pathways to the IV pump system 54. Preferably the IV pump system 54 is a multi-channel IV pump system adapted to regulate flow from the various sources, such as potential multiple drug sources 50 and fluid sources 52. The patient arm 56 is in fluidic contact with the IV pump system 54 for delivery of the drug from drug source 50. A manifold 58 is shown included within the dashed lines. The manifold includes a fluid port 62 adapted to receive output of the fluid source 52 as regulated by the IV pump system 54. A patient port 64 provides connection to the patient arm 56 via a tube comprising a fluidic connection. The patient port 64 alternately provides output of fluid initiating at the fluid source 52 to the patient arm 56, and at alternate times, receives blood from the patient arm 56 as input to the manifold 58. The fluid port 62 is connected to the patient port 64 via a fluid pathway 66. A sample line 68 is connected to the fluid pathway 66. Preferably, the sample line 68 forms a T-intersection with the fluid pathway 66 at intersection node 70. The sample line 68 provides fluidic transport of materials from the fluid pathway 66 to an analysis system. Optionally, the sample line 68 terminates in an analyzer interface port 72. Optionally, a disposal port 74 may be provided as input to the manifold 58 adapted to receive waste output from the analyzer 76.

Transfer of fluids through the manifold 58 is controlled by operation of the IV pump system 54 and additional pump forces. Such additional pump forces may be provided by a pump 78 or, in the alternative or in addition thereto, a vacuum source 80. In this embodiment, the pump force is supplied so as to selectively receive materials from the disposal port 74 and the fluid pathway 66. The pump force is supplied to the fluid pathway 66 via a pump connection 82. The pump connection 82 preferably forms a T-connection with the fluid pathway 66. The fluid flow within the manifold is also controlled by operation of valves. A upstream isolation valve 84 is preferably disposed on the fluid pathway within the manifold 58 downstream of the fluid port 62. A patient shut-off valve 86 is preferably located in the fluid pathway 66 upstream of the patient port 64 and downstream of sample line 68. A analyzer access valve 88 is preferably disposed adjacent the intersection node 70, preferably on the sample line 68. A disposal valve 90 is interposed between the disposal port 74 and the pump force source. A pump force valve 92 is disposed between the pump force and the fluid pathway 66, optionally with some section of the pump connection 82 disposed between the pump force valve 92 and the fluid pathway 66.

In one aspect of this invention, a detector 94 is preferably positioned to determine the position of fluid or blood within the manifold 58. In the preferred embodiment the detector 94 is positioned adjacent the fluid pathway 66 between the upstream isolation valve 84 and the intersection node 70. More particularly, if a pump force is supplied directly to the fluid pathway 66, as shown, the detector 94 is preferably positioned between the intersection of the pump connection 82 and the intersection node 70. Any form of detector 94 consistent with the objects of this invention may be utilized. The preferred detector utilizes optical changes in the contents of the fluid pathway 66 to detect a change. For example, an optical detector 94 may detect the blood/saline interface when that interface is adjacent the detector 94. An ultrasonic detector may be used to detect the presence of fluid in line 66.

In operation, the system may be operated wherein the patient receives fluid, such as saline, from the fluid source 52. In that event, the fluid is received at the fluid port 62 and transferred through the fluid pathway 66 and output at the patient port 64 with valves 84 and 86 being open. Ordinarily, this may occur simultaneously with infusion of the drug from the drug source 50. To perform a measurement, drug flow is preferably terminated, so as to permit more accurate reading of the patient state. To sample blood from the patient, the upstream isolation valve 84 is closed and the pump force applied to the fluid pathway 66. In the disclosed embodiment, the pump 78 provides a pumping force on pump connection line 82 via now opened pump force valve 92. This causes the sample to be drawn through the patient port 64 past now opened patient shut-off valve 86. The pump 78 provides the removed saline to the disposal container 80. The blood is drawn at least to intersection node 70, and preferably to detector 94. Once sufficient blood has been drawn, the blood is then taken from the intersection node 70 through the sample line 68 to the analyzer 76. In one embodiment, the blood is pushed through the sample line 68 by closing the patient shutoff valve 86, opening the analyzer access valve 88, closing the pump force valve 92 and opening the upstream isolation valve 84. This combination permits material from the fluid source 52 to be pumped by IV pump system 54 through the upstream portion of fluid pathway 66 to cause flow of the blood slug up through the sample line 68. Advantageously, if the blood slug has a leading edge disposed upstream of intersection node 70, the blood in the sample line 68 is taken from the non-leading edge of the blood slug in the fluid pathway 66. Alternatively, the blood may be drawn from intersection node 70 by a pump force applied to sample line 68 directed towards analyzer interface port 72. In the embodiment shown, analyzer 76 receives a blood sample from the analyzer interface port 72. A sample nozzle 96 serves to deliver the blood to the test unit 98. Optionally, the sample nozzle 96 may be placed in apposition to the disposal port 74 to dispose of the leading edge of the blood slug which travels through sample lines 68. The sample nozzle 96 may then deliver a clean blood sample to the test unit 98. After the blood is delivered to the test unit 98, the manifold 58 may be flushed with saline, serving also to clean the sample nozzle 96. Disposal of this material from the sample nozzle 96 is via the disposal port 74. The remaining patient blood in the manifold and connection from the patient port 64 to the patient arm 56 may be returned to the patient.

FIG. 3 shows a planned view of a valve arrangement which permits selective delivery of the blood sample to an analyzer or to the continuation of a blood circuit. A rotational valve 200 receives as input from path 202 a blood sample. In one orientation of the rotation valve 200, the pathway 202 is connected to an output path 204. When the rotational valve 200 is rotated 90° (counter-clockwise in FIG. 3) the rotational valve 200 provides connection from the pathway 202 to the analyzer (not shown). By rotation of the valve 200, blood may be directed to the analyzer (such as an APPT cartridge) or to a waste cartridge by a simple rotation.

Figure 4:
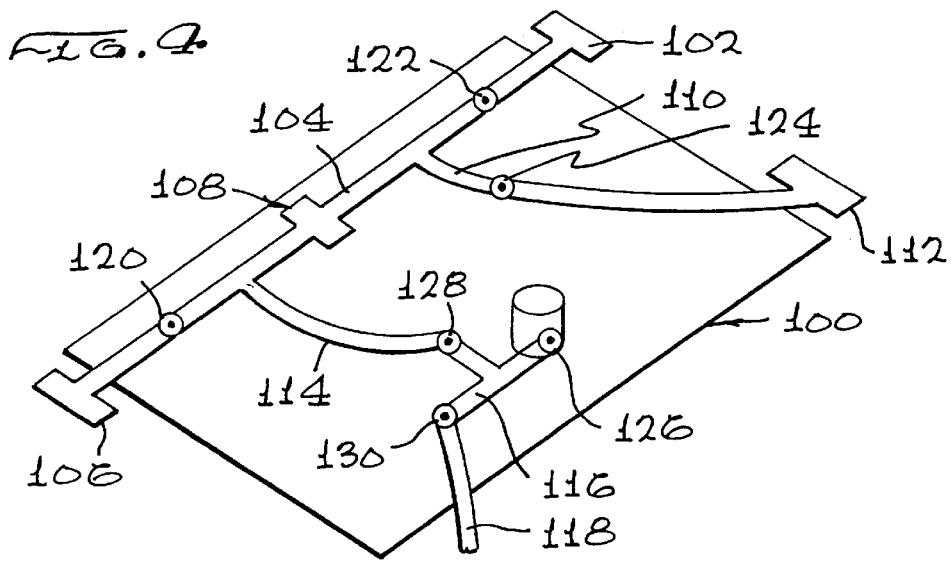
FIG. 4 shows a perspective view of an integrated manifold.

FIG. 4 shows a perspective view of an integral manifold assembly. The manifold 100 is preferably formed from plastic, such as polycarbonate, ABS, SAN, StyroliteTM, or other suitable material which is sterilizable, including gamma, electron beam and ethylene-oxide sterilizable. The tubing is preferably a material which does not promote heparin binding (e.g., a teflon tube, or PVC or polyurethane tube with covalently linked heparin). Tubing size is selected to prevent hemolysis of the blood. A patient port 102 is connected to a fluid pathway 104 which couples to a fluid port 106. A detector 108 is optionally located on the fluid pathway 104. A sample line 110 is coupled to the fluid pathway 104, terminating in a analyzer interface port 12. A pump connection 14 connects to the fluid pathway 104. A pump force is supplied to vacuum region 116. The vacuum force in vacuum region 116 may be supplied by any known manner consistent with this invention, including but not limited to use of a peristaltic pump, a vacutainer, or a linear pump or a vacuum pump such as formed through a syringe having a linear force applied to the syringe. Optionally, if the vacuum force is generated by a vacutainer, a spike 1 8 may be utilized to interface the vacutainer. The spike 118 may also serve as a connection for disposal. A upstream isolation valve 120, a patient shut-off valve 122, a analyzer access valve 124, a disposal valve 126 and pump force valve 128 are utilized as described in connection with the similarly named valves in FIG. 2. A vacuum valve 130 optionally provides selective interconnection of the vacuum source with the manifold 100.

The feedback controlled delivery of heparin occurs in a "data poor" environment. Measurements of patient status cannot be obtained on a frequent basis. In the preferred embodiment, the infusion rate calculated by the control algorithm is based on a pharmacodynamic (PD) model of the heparin response. Since there is a large patient variability with heparin, there are a number of parameters in the PD model which describe the individual response. Based on measurements of patient response, the model parameters can be adjusted. Since the measurements are sparse and subject to some uncertainty, the patient parameter estimates will have a certain confidence interval which will affect the expected control accuracy. The information utilized includes population parameter values, including values of the variance and values for measurement accuracy. Sample scheduling may be optimized, though the system imposes certain limits on the frequency of measurement (such as cost and limited number of cartridges). The control system optionally determines when additional information from a new measurement would be most beneficial based upon observed patient response, history of infusion adjustment, desired control level accuracy, and confidence of model parameters.

Figure 5:
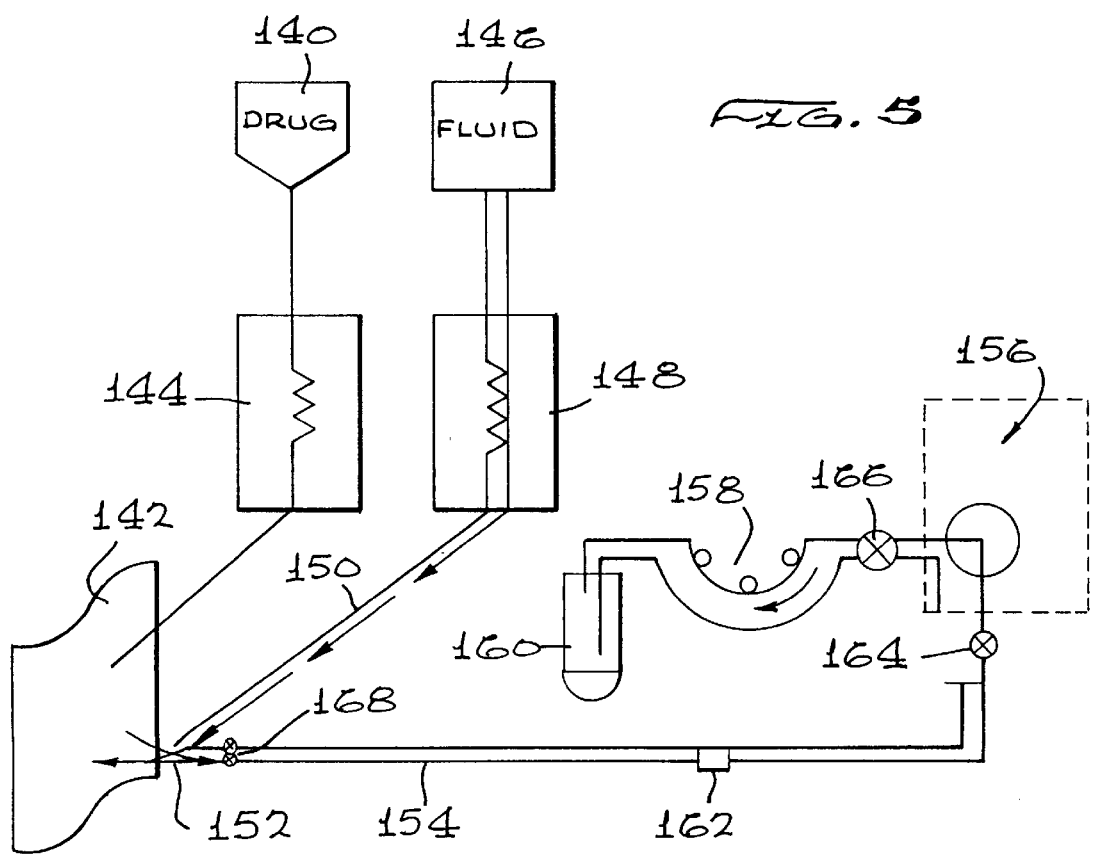
FIG. 5 shows an alternate fluidic system.

FIG. 5 shows a schematic view of an alternative fluidics arrangement to those shown in FIGS. 2 and 3. The drug source 140 is controllably connected to the patient arm 142 via pump 144, as described previously. The fluid source 146 is selectively connected to the patient arm 142 through pump 148. Delivery tube fluidic path 150 is connected to the patient arm 142, preferably via a Y-connector 152. The Y-connector 152 additionally connects to the sample path 154. The sample path 154 is operatively connected to the sampler system 156. A vacuum force is supplied to sample path 154, such as by operation of a peri-pump 158. Disposal is by any means desired, such as through a vacutainer 160. Optionally, a detector 162 may be utilized, in the preferred embodiment the detector 162 as shown comprising an optical window for use in conjunction with an optical detector. A sample system valve 164 serves to isolate the sample path 154 from the sampler system 156. A pump valve 166 serves to isolate the pump force, such as created by the peri-pump 158 from the sampler system 156.

In operation, sampling occurs by terminating drug delivery and flowing fluid from the fluid source 146 through the pump 148, through the Y-connector 152 through the sample path 154. Optionally, a check valve or electronically controlled valve is used. The fluid flow is aided by pump force a supplied by the pump 158, with valves 164 and 166 being open. The pump 148 is then turned off, resulting in the drawing of patient blood. Optionally a check valve 168 is utilized to control the fluid and blood flow. The blood is then pumped through the sample path 154. When the blood passes detector 162 the system may utilize that time and pump rate to calculate the necessary pumping time to cause delivery of blood to the sampler system 156. Once the sample has been delivered to the sampler system 156, flow of saline via the pump 148 may be utilized to provide a flushing source of fluid from the source 146 through the sample path 154. Once the sample is delivered to the sampler system 156, it may be analyzed and the data used in the feedback controlled control system.

Figure 6A:
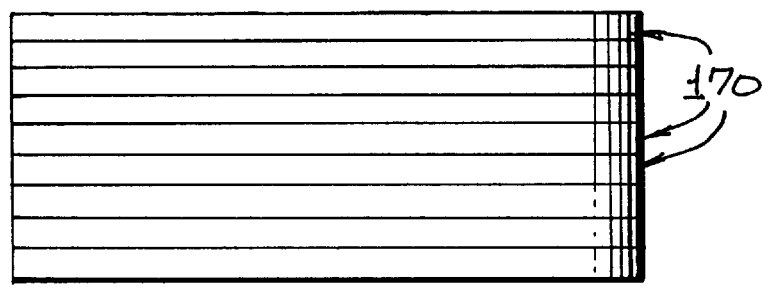
FIG. 6A shows a end-on view of a stacked multiple test unit system.
Figure 6B:
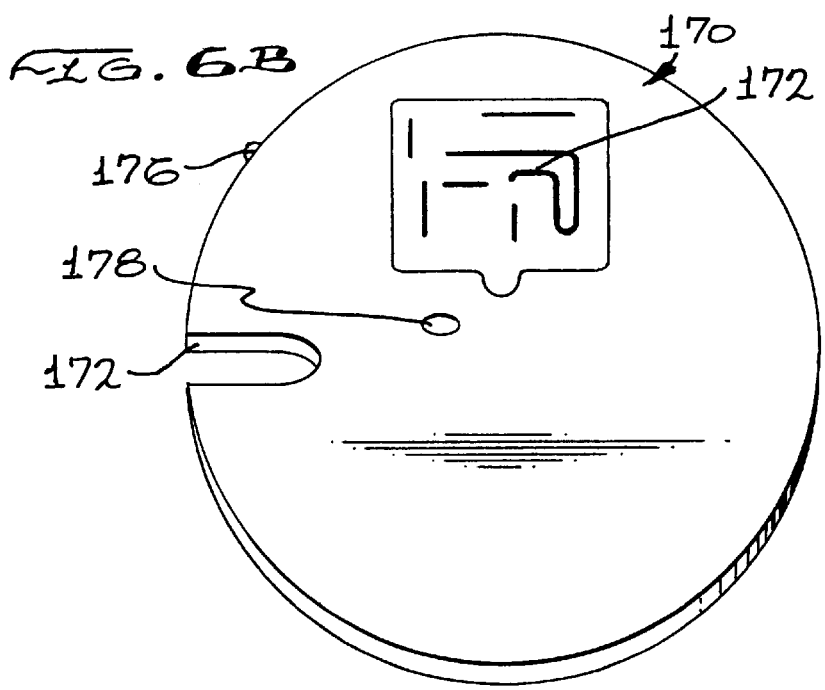
FIG. 6B shows a perspective view of an individual test disk for use in a multiple test unit.

FIG. 6A shows a side view of multiple stack test units. Each test unit 170 comprises a test site 172 onto which the biological material to be analyzed is supplied. This test may include any of the desired tests, such as for monitoring of the coagulation state the APTT test such as manufactured by Boehringer Mannheim Diagnostics, Cardiovascular Diagnostics Inc. or International Technidyne Corporation. Alternative tests include the activated clotting time (ACT), Factor X or Xa, partial thromboplastin time tests, whole blood clotting time tests, or any general heparin assay.

Optionally, the test unit 170 may include a key way 174 to assist in orientation of the unit 170 during loading. Optionally, nesting dimples 176 may be provided to promote stacking of the test disks 170. A blood drop opening 178 may be provided for access to the test location 172.

Figure 7:
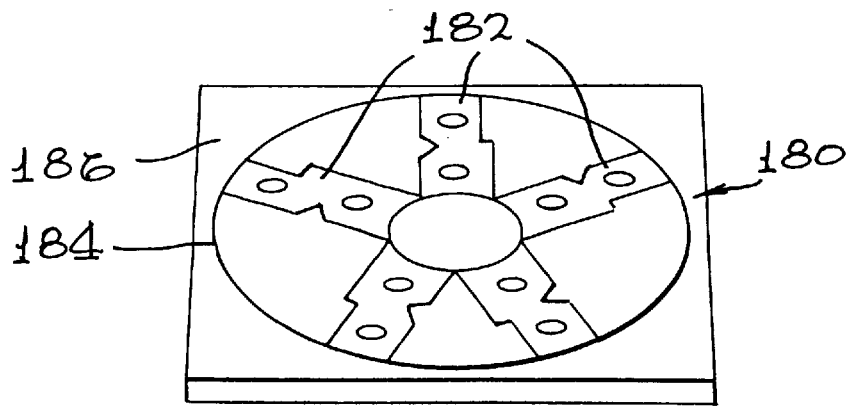
FIG. 7 shows a perspective view of a planar carousel arrangement for multiple test site locations.

FIG. 7 shows a perspective view of a planar carousel arrangement comprising multiple test units. A carousel 180 includes multiple test units 182 (five being shown in FIG. 7). The individual test units 182 are arranged symmetrically around an axis of rotation for the carousel 180. The individual test units 182 are mounted on a platen 184 which permits rotation of the platen relative to the housing 186.

Figure 8A:
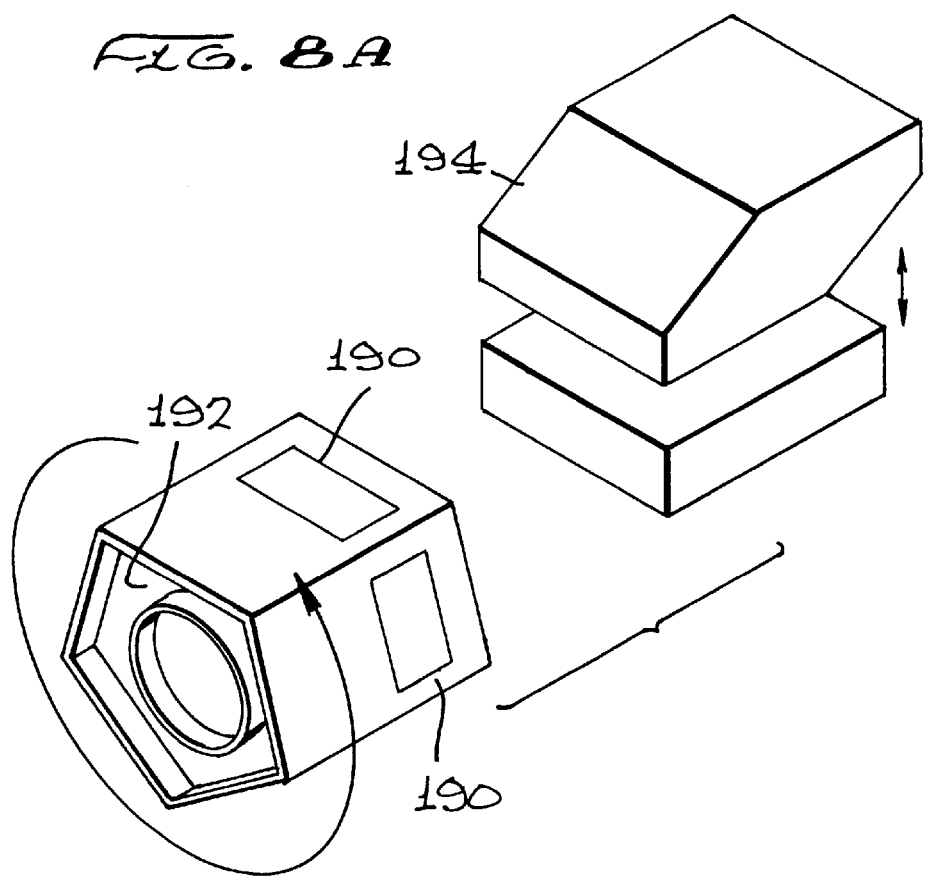
FIG. 8A shows a perspective view of a multiple test site location carousel.
Figure 8B:
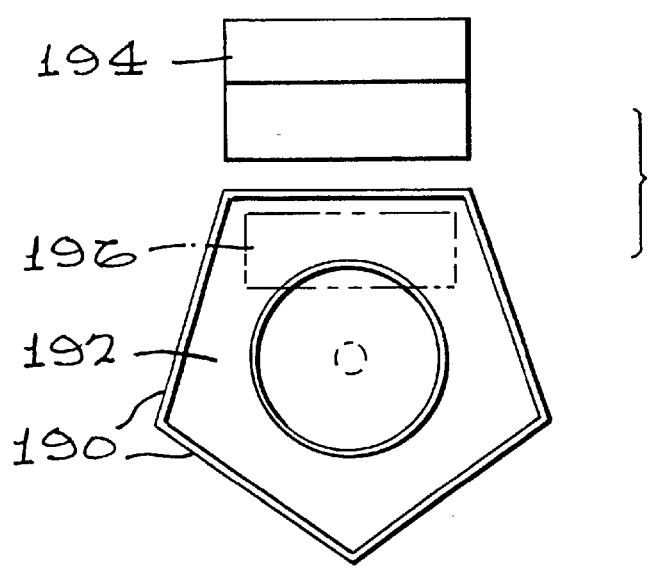
FIG. 8B shows an end-on view of the structure of FIG. 8A.

FIGS. 8A and 8B show views of an alternative arrangement for providing multiple test units to a detector. Test units 190 are affixed to a housing 192 presenting sequential faces to a reader head 194. In the embodiment shown, the cartridge 192 includes five faces on which test units 190 may be disposed. The cartridge 192 has an axis of rotation permitting sequential apposition of a test unit 190 with the reader head 194. An arrow indicates the rotational motion of the cartridge 192 relative to the reader head 194. Optionally, a heater 196 may be utilized to aid in the testing process as performed by the test unit 190.

FIGS. 9A and 9B show a top view and side view of a multiple test cartridge container. A cartridge 210 serves to contain multiple individual test chips 212. The cartridge 210 serves to contain the chips 212 in a stacked arrangement. An arm 214 causes displacement of the chip 212 from the cartridge 210 to a test stage 216. The chip 212 on the test stage 216 receives a blood drop upon which analysis is performed. Once the test is completed, the chip 212 is reinserted into the cartridge 210. Preferably, the cartridge 210 is formed with two chambers, an upper chamber 218 which contains the unused chips 212 and a lower chamber 220 who contains the used chips 212. The used chip 212 is removed from the test stage 216 by optional lowering of the test stage 216 relative to the cartridge 210, with optional lateral force applied to the chip 212 to cause the used chip to be inserted into the lower chamber 220.

FIG. 10 shows a perspective view of a multiple test cartridge system in which multiple individual test locations 230 are disposed laterally adjacent one another. Each individual test location 230 may be mounted on a substrate 232 or merely formed adjacent to each other, resulting in a unitary structure. Optionally, a bar code 234 is disposed on the multiple test cartridge system. In one embodiment, the bar code 234 may contain information indicative of the specific activity of the tests. For example, if APTT tests are utilized in such a system, the tests tend to vary from manufacturer to manufacturer, and are even subject to different results being reported by different operators. The automated system of this invention permits the encoding of information (such as through the bar code) to indicate to the system the amount by which the test results must be corrected so as to provide a standardized result.

In one aspect of this invention, the system may be provided with test units to measure both the coagulation state (such as through the use of an APTT test) and the prothrombin (PT) time. Such combinations are particularly useful when a patient is being transitioned from a heparin IV administration to Warfarin, during which time the APTT measurements are affected by the presence of the Warfarin. Difficulty in titration of heparin is incurred at this time. By providing separate measurements of PT and APTT, the system may correct for the presence of Warfarin and administer desirable amounts of heparin, and determine the optimum dose of Warfarin.

Figure 11:
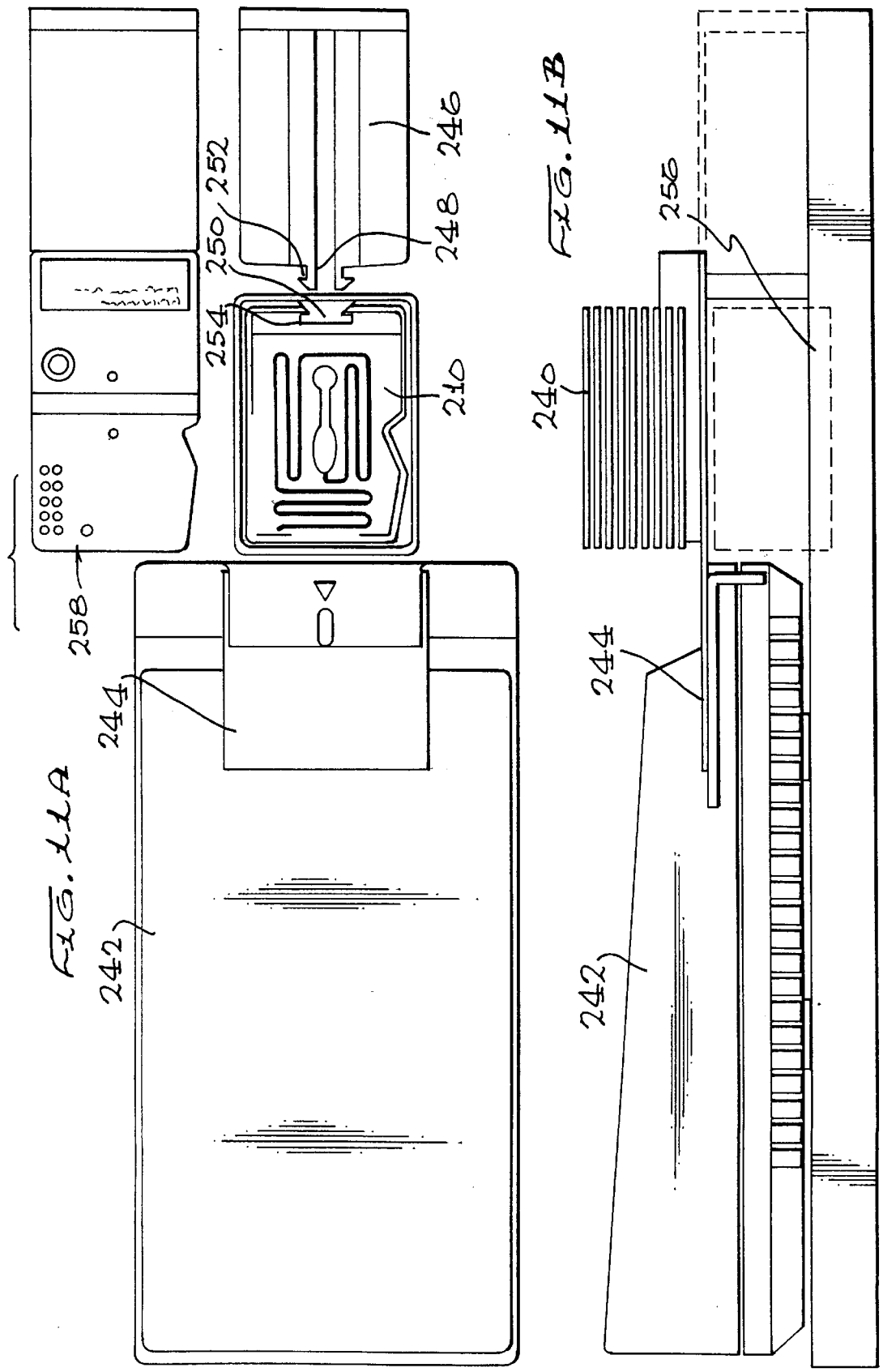
FIG. 11A shows an alternative slidetray arrangement in top view.
FIG. 11B shows an alternative slidetray arrangement in side view.

FIGS. 11A and B show a top view and side view, respectively, of an alternative arrangement for a multiple test cartridge container. One or more chips 240 may be arranged in a stacked configuration. One chip 240 at a time is inserted into the test unit 242 on to the test stage 244. In this embodiment, the arm 246 moves the chip 240 into use position on the test unit 242 test stage 244. Once the test is completed, the arm 246 retracts, drawing the now used chip 240 from the test stage 244. In the preferred embodiment, the used chip 240 is disposed of into a receptacle 256 through gravity. In one embodiment, a key system provides locking engagement between the arm 246 and the chip 240. This permits withdrawal of the used chip 240 from the test stage 244. The arm 246 includes a key 248 at the terminal end of the arm 246. The key 248 serves to mate with the lock 250 to provide retraction force to the used chip 240. In the preferred embodiment, moveable latches 252 are adapted to mate with recesses 254 in the key 250. Preferably, the FIGS. 252 flex, such as towards the center line of arm 246 to positively lock with the key 250. After the chip 240 has been used and removed from the test stage 244, the used chip 240 drops to receptacle 256 as the key 248 separates from the lock 250.

Optionally, a quality control or calibration chip 258 may be inserted into the test unit 242 for calibration or quality control purposes. In one embodiment, the chip 258 may be moved relative to the test unit 242 and then inserted into the test stage 216. Such action ensures the continued calibration or proper operation of the test unit 242.

Figure 12:
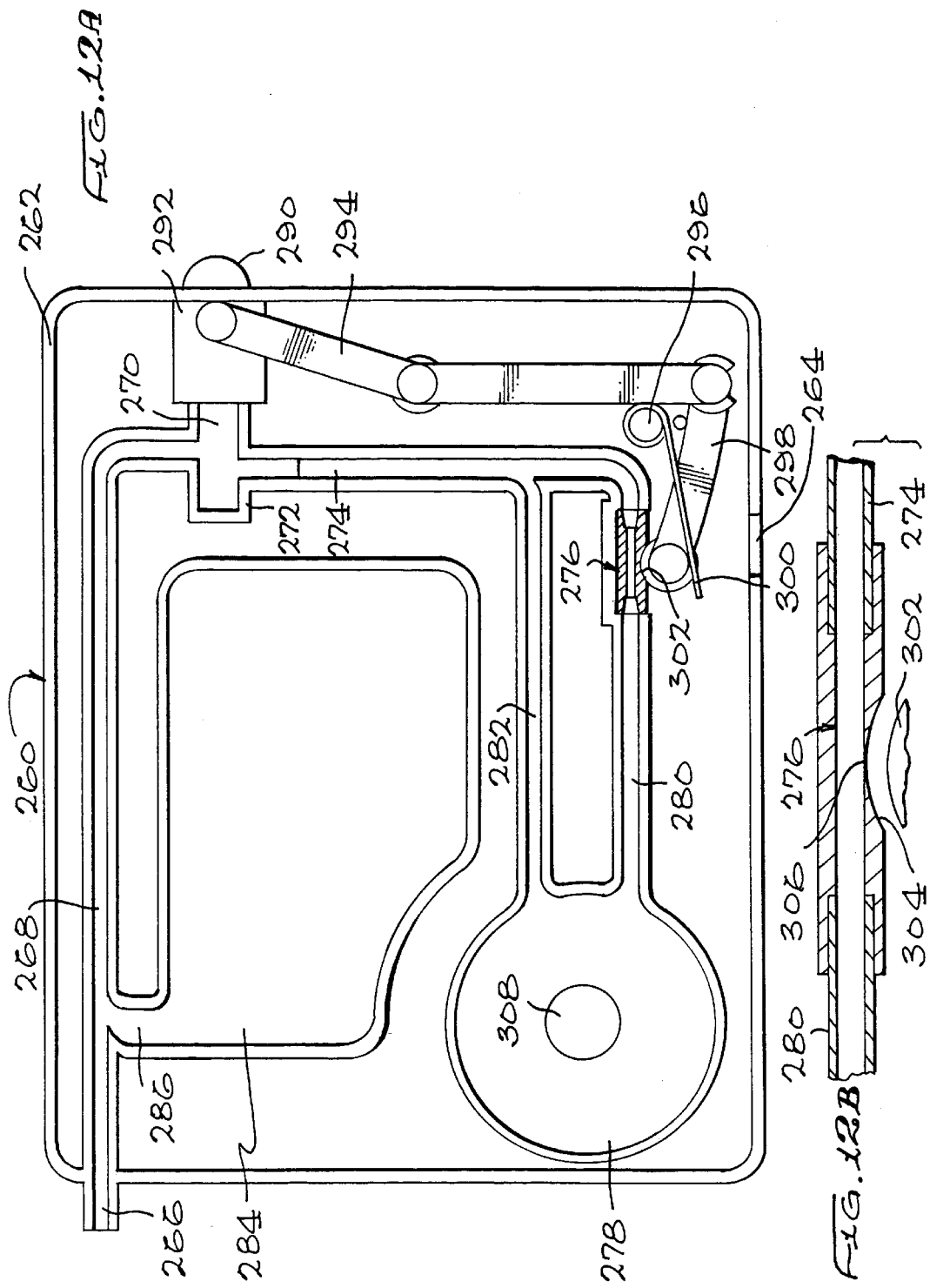
FIG. 12A shows an integrated assembly in top view.
FIG. 12B shows a detail of the closeable blood delivery opening of FIG. 12A.

FIGS. 12A and 12B show top and detail views, respectively, of an integrated assembly for the receipt, sequential delivery of blood drops, and storage of waste material. In the preferred embodiment, the assembly 260 includes an outer housing 262 which includes an aperture 264 adapted to provide blood to an analysis unit (see, e.g., chip 240 in FIG. 11A). The assembly 260 includes an inlet 266 for receipt of blood or other fluid, which is connected via an input tube 268 to a first input valve 270. A delivery tube 274 connects to a delivery unit 276 to be described in detail later. The delivery unit 276 is operatively connected to pump 278 such as by a pump input 280. The output of the pump 278 is connected by a pump output 282 to a receptacle 284 via an input 286. The connection from the pump output 282 is disposed in part below the input tube 268 and is obscured in FIG. 12A.

The delivery unit 276 is designed for the selective delivery of a measured amount of blood or other material. In the preferred embodiment, an actuator 290 is moved relative to the housing 262 to cause the sleeve 292 to move the pivot arm 294. The pivot point 296 bears upon the pivot arm 294, causing the arm 298 to move away from the delivery unit 276. Optionally, a spring 300 provides a restoring force to cause the arm 298 to seal with the delivery unit 276. The arm 298 terminates in a closure member 302 causing the delivery unit to seal.

The delivery unit 276 is shown in cross-sectional detail in FIG. 12B. Preferably, the delivery tube 274 and the pump input tube 280 are connected to a delivery unit 276. The delivery unit 276 in one embodiment includes a cut-out 304 adapted to sealingly engage the closure 302. of blood or other formed with an aperture 306 to permit flow of blood or other fluid from the delivery unit 276. When blood or other materials are to be delivered through the housing aperture 264, the closure 302 moves away from the delivery unit 276. Preferably, the closure 302 may be disposed in the flow path between the delivery unit 276 and the housing aperture 264 to permit washing of the arm 298, particularly the closure 302.

In the preferred embodiment, the pump 278 consists of a roller-type peristaltic pump. In the preferred embodiment, the pump 278 is integrated with the assembly 260. In one embodiment, a driving rotor mates at hub 308 to drive the peri-pump.

Figure 13:
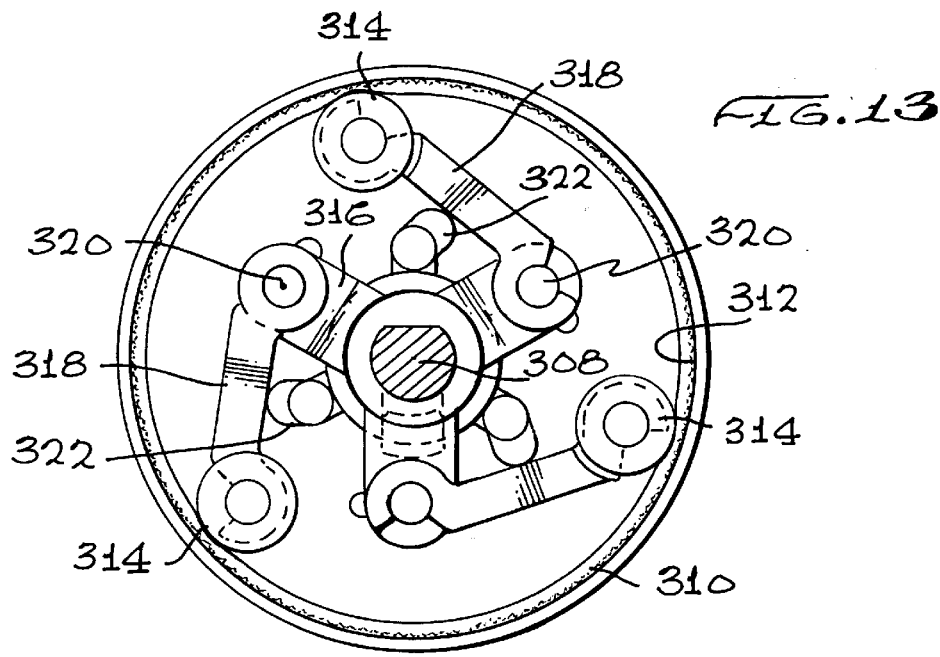
FIG. 13 shows a plan view of the roller mechanism of the peri-pump.

FIG. 13 shows a preferred embodiment of the pump 278 in detail in plan view. A tube 310 is provided adjacent the housing innercircumference 312. The tubing 310 in actuality connects to an input and output, such as the pump input 280 and pump output 282, respectively. Rollers 314 press against the tube 310, and when driven rotationally around hub 308 cause fluid in the tube 310 to move.

In one aspect of this invention, the rollers 314 are adapted for motion towards and away from the hub 308. The rollers 314 may be moved from their operational, fully extended, position adjacent the tube 310, such as prior to use of the pump 378. This is advantageous in that the tubing 310 may then be sterilized with ethylene oxide and avoids deforming the tube 310. One structure for achieving radial motion of the rollers 314 is through first arms rigidly connected to the driving hub 308 and arranged in a radial direction. Conventionally, three rollers 314 are used, though the number may be varied. Each of the preferably three first arms 316 are connected to second arms 318 which are rotatable around axis 320. Cam 322 selectively moves second arms 318 so as to cause the roller 314 to move towards and away from the housing innercircumference 312.

Figure 14:
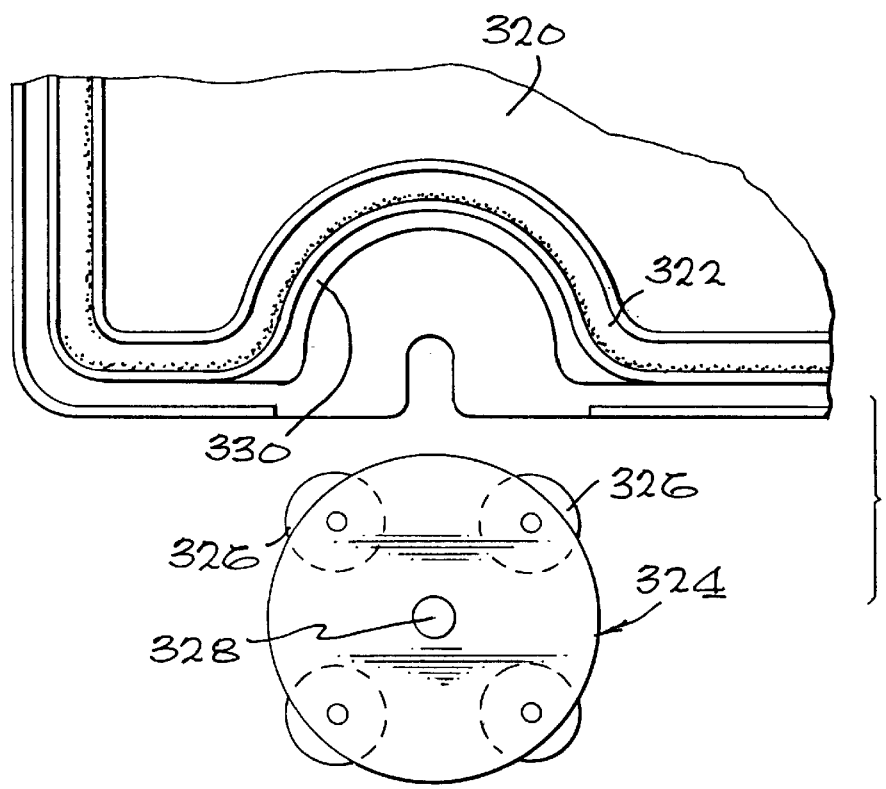
FIG. 14 shows a plan view of a roller mechanism and assembly.

FIG. 14 shows a plan view of an alternative arrangement for interfacing a peristaltic pump with the assembly. A housing 320 includes within it a tube 322 which is adapted to carry a fluid, such as blood. A peri-pump rotor 324 includes rollers 326 and a hub 328. The rotor 324 is adapted for motion towards the housing 320 so as to conform to a indentation 330 in the housing 320. In operation, the rotor 324, rollers 326 and hub 328 are moved into the space 330 so as to press upon the tube 322 to achieve pumping action through rotation of the hub 328.

FIG. 15 presents an alternative preferred embodiment of the present invention. In this embodiment, a therapeutic solution such as heparin 300 is delivered to a patient 310 intravenously via a feedback controlled drug delivery system. This feedback control drug delivery system allows for the automated infusion and periodic sampling and testing of a patient's blood without operator intervention. Further, the system allows a single catheter 311 to be placed in the vein of a patient with the drug infused through this catheter 311 and at a later time, blood sampled from this same catheter 311. Such a system allows an operator to set a desired level of a drug or drug effect to be present in a patient's bloodstream. The system allows for direct measurement of drug concentration, or alternatively, the system to measure the effect of the drug in the sampled blood. For example, a preferred embodiment of the present system measures the time for blood to coagulate thus indicating the effect of the anti-coagulant drug such as heparin. The system calculates an initial rate to begin drug infusion and infuses the drug for a period of time. At a predetermined time, the system changes modes to allow blood to be sampled and tested. Based on the level or effect of the drug found in the bloodstream, the system adjusts the rate of the drug infusion, thus titrating the drug to the desired level or effect.

This preferred embodiment has at least one therapeutic solution such as heparin 300 and/or a flushing solution such as saline 302. Although in this embodiment the therapeutic solution is heparin and the flushing solution saline, those skilled in the art will recognize several alternatives to these solutions.

The heparin 300 and the saline 302 are connected to the fluid delivery pumps 304 and are connected to a heparin supply tube 352 and a saline supply tube 354 respectively. The heparin supply tube 352 has a check valve 351 before connecting to the saline supply tube 354 at the fluid tube junction 353. The fluid tube junction connects to a sample tube junction 320. Although this embodiment shows two separate pumps, those skilled in the art will recognize that multichannel pumps are available that can pump multiple tubes. Additionally, saline 302 is attached through the fluid supply tubes 306 but those skilled in the art recognize that saline 302 is optional. Further, those skilled in the art will recognize that syringe pumps, gravity pumps, or other devices are available to deliver a fluid through an IV. The fluid delivery pumps 304 are well known in the art and are capable of volumetric control of one or more IV tubes thereby controlling the delivery rate of one or more drugs. The fluid delivery pumps 304 are controllable from an electronic controller 336. Further, the fluid delivery pumps 304 may communicate with the controller, including communicating delivery status information.

A bidirectional patient tube 322 connects the sample tube junction 320 to the patient 310. More specifically, the bidirectional patient tube 322 terminates in a catheter 311 which is intravenously placed in the patient 310. Therefore, the fluid delivery pump 304 may pump heparin 300 through the fluid supply tube 306 and the bidirectional patient tube 322 to be infused intravenously into the patient 310.

This preferred embodiment also contains an analyzer 312 which communicates with the controller 336. Those skilled in the art will recognize that the controller 336 may be external to the analyzer 312 as shown in FIG. 15 or may be incorporated within the analyzer 312. A sample tube 318 connects the analyzer 312 to the sample tube junction 320. The sample tube 318 has a clamp housing 316 and a blood dropper 328 at its terminus.

When in use, the sample tube 318 extends from the sample tube junction 320 through the analyzer 312, with the clamp housing 316 set in the clamp housing holder 314 with a portion of the sample tube 318 extending around a peristaltic pump 324, occluding the sample tube 318. The peristaltic pump 324 is configured such that a platen arm 334 positions the sample tube 318 in compressioned contact with at least one roller 336 of the peristaltic pump 324. As the peristaltic pump 324 rotates the peristaltic pump 324 draws fluid through the sample tube 318 towards the analyzer, with the fluid being pushed out the blood dropper 328.

The fluid supply tube 306, the bidirectional patient tube 322, and the sample tube 318 comprise the sample/supply set 308 shown in FIG. 16. The sample/supply set 308 of the preferred embodiment is a medical disposable unit that is used for a single use. That is, each patient serviced by the preferred embodiment requires a new, sterile sample/supply set 308. The sample/supply set 308 will be described in more detail below. Additional components of the preferred embodiment will be introduced and described while now presenting modes of operation.

This preferred embodiment has four modes of operation: 1) infuse mode; 2) sample mode; 3) analyze mode; and 4) clear mode. Each mode is addressed separately below.

In mode one, infuse mode, the controller 336 instructs the fluid delivery pump 304 to pump heparin 300 into the heparin supply tube 352. The fluid flows from the heparin 300 fluid supply, through the heparin supply tube 352 toward the sample tube junction 320. In the infuse mode, the peristaltic pump 324 of the analyzer 312 is not rotating and the platen arm 334 is pressed tightly against one or more of the rollers 336, thus occluding the sample tube 318. Therefore, the heparin 300 flowing through the heparin supply tube 352 flows through the sample tube junction 320 into the bidirectional patient tube 322 and via the catheter 311 into the patient 310. In a similar manner, the preferred embodiment may deliver saline 302 to the patient 310. Further, the saline 302 and heparin 300 can be infused individually or simultaneously. The rate of infusion is set by the controller. When the controller or the user indicates it is time to take and analyze a new sample, mode two begins.

In mode two, sample mode, the preferred embodiment first flushes the system. The heparin pump 304 is first turned off and the saline pump activated. Those actions pump saline 302 through the saline tube 354, sample tube junction 320, the bidirectional flush tube 322, and the catheter 311, and to the patient 310. Once the flush path from the fluid tube junction 353 to the patient 310 is cleared of heparin, the peristaltic pump 324 is activated at a rate somewhat less than the rate of the saline pump 304. Then, the peristaltic pump 324 draws saline from the sample tube junction 320 through the sample tube 318, and out the blood dropper 328, cleaning the sample tube 318 of heparin. Since the saline pump 304 is pumping a rate faster than the peristaltic pump, a small quantify of saline is still being pumped to the patient 310. With the system now cleared of heparin, all pumps are stopped.

After flushing the system, the preferred embodiment inflates the pressure cuff 307, which is placed around an extremity and near the intravenous entry point of the patient 310. As the intravenous entry point is often the arm or hand, the pressure cuff may be placed on the upper arm. It is well-known in the art that the pressure of an inflated pressure cuff assists in the drawing of blood.

With the cuff inflated, the preferred embodiment now takes a fluid sample, generally blood, from the patient 310 and draws the blood sample to the analyzer 312. In this mode, the fluid delivery pump 304 is not operational so no therapeutic solution is being pumped through the fluid supply tube 306. The peristaltic pump 324 rotates (clockwise as illustrated) and as each roller 336 contacts the sample tube 318, that roller 336 pushes fluid in the sample tube toward the blood dropper 328. The blood dropper 328 is positioned on a blood dropper arm 340, which moves the blood dropper 328 from a standby area to a position above a waste container 338. With the blood dropper 328 positioned over the waste container 338, fluid pushed through the sample tube 318 is deposited in the waster container 338. As the peristaltic pump 324 turns, a bolus of blood is pulled from the patient and up the bidirectional patient tube 322 toward the analyzer 312.

As the peristaltic pump 324 continues to operate, the bolus of blood reaches the clamp housing 316. The clamp housing 316 may contain an optical sensor to detect the leading edge of the blood sample. Since the volume of fluid in the sample tube 318 after the clamp housing 316 is known, and the volume moved by the peristaltic pump 324 is also defined, it can be calculated how much the peristaltic pump 324 must rotate until the blood has reached the blood dropper 328. Alternatively, if no optical sensor is used, the peristaltic pump 324 is rotated a sufficient number of times to bring the blood from the patient 310 to the blood dropper 328.

After the blood sample is at the blood dropper 328, the peristaltic pump 324 stops. As a drop of blood may be left hanging from the blood dropper, the peristaltic pump 324 can be rotated in the opposite direction a small amount to draw the blood drop back into the blood dropper 328. The blood dropper arm 340 now moves to place the blood dropper 328 over the test area 330. As the sample mode ends the pressure cuff is deflated.

Mode three, the analyze mode, now begins. The analyzer 312 has a slide cassette 332 which is vertically positionable. The slide cassette 332 holds several slides 346, with each slide having at least one area that has a reagent which reacts with a substance that may be present in the patient's blood sample. The cassette 332 is positioned vertically such that a slide arm 326 contacts the desired slide 346 in the cassette 332. The slide arm 326 pushes the slide 346 and positions it into the test area 330. The peristaltic pump 324 is activated for a short time, pushing a small amount of blood from the blood dropper 328 into the test area 330.

Referring to FIG. 22, this small amount of blood falls to the slide 346 onto the blood dropper area 349. A capillary channel 351 leads from the blood dropper 349 to a vent hole 411. The action of capillary channels are well known in the art. The capillary channel 351 or a chamber in the capillary channel has a reagent area 347 that contains a reagent selected to react with a target substance. As the blood is drawn through the capillary channel 351, the target substance in the blood begins to react with the reagent at the reagent area 347. The target substance is generally the therapeutic fluid that is being infused, which in the preferred embodiment is heparin 300. A sensor, generally an optical sensor, in the test area 330 detects any change on the slide due to the presence of heparin.

In the preferred embodiment, the reagent area 347 has a reagent that reacts with blood to speed the clotting process of blood. Since the preferred embodiment infuses heparin, a drug which inhibits drug clotting, the amount of clotting activity in the reagent area 347 will relate to the effectiveness of heparin in the blood sample. Indeed, as blood flows from the capillary channel 351 into the reagent area 347, the blood begins to clot until finally, the clotting action causes no more blood to pass through the reagent area 347. The preferred embodiment has a light source, typically a low-power laser, which is directed through the capillary channel 351 and detected by an optical sensor. If blood is moving in the capillary channel 351, the optical sensor detects the motion of the flowing blood cells, but if the blood has clotted anywhere in the capillary channel 351, the blood will not be moving and the optical sensor will not detect the motion of any blood cells. The time it takes the blood to clot in the capillary channel is a measurement that relates to the effect the heparin is having on the patient's blood.

Once the analyzer 312 has determined the effectiveness of the heparin in the blood sample that information is passed to the controller 336. The controller 336 uses the information received from the analyzer 312 to adjust the quantity or rate of the heparin delivery from the pump 304 during the next infusion cycle. With the analysis complete, the system moves into mode four.

In mode four, the system is cleared in preparation for a new infusion mode. In clear mode, the blood dropper arm 340 is moved such that the blood dropper 328 is once again positioned above the waste container 338. Both the peristaltic pump 324 and the fluid delivery pump 304 controlling a flushing solution such as saline 302 are turned on. With both pumps operating, saline 302 is pumped by the fluid delivery pump 304 through the fluid supply tube 306 to the sample tube junction 320. Since the peristaltic pump 324 is also operational, saline 302 will be pulled through the sample tube 318. The optical sensor in the clamp housing, if present, will detect the trailing edge of the blood, with the controller 336 then calculating how much the peristaltic pump 324 needs to rotate to force all the blood through the blood dropper 328 into the waste container 338. Further, since the pump 304 pumps at a faster rate than the peristaltic pump, saline is also pumped toward the patient. This acts to flush blood out of the bidirectional patient tube 322 and the catheter 311.

Once the sample tube and the catheter 311 have been flushed of blood, the preferred embodiment is ready to go back to mode one, the infusion mode. In the next infusion mode, the quantity of therapeutic solution 300 delivered by the fluid pump 304 will be adjusted by the controller 336 based upon results received from the previous test performed by the analyzer 312.

With the elements and functionality of the alternative preferred embodiment generally described, selected elements will be individually described in greater detail.

FIG. 16 details the sample supply set 308. The sample/supply set 308 provides an interconnect between one or more fluid sources, a patient and an analyzer as described above. The sample/supply set 308 of the preferred embodiment comprises a heparin fluid supply tube 352 and a saline fluid supply tube 354. Each of these supply tubes, 352 and 354 connect to their respective fluid sources through a fluid supply connector 356.

The fluid supply source (300/302) is generally a bag connected to an IV tube which is placed in a IV pump. The IV tube from the bag passes through the pump and terminates with a Leur fitting which connects to the fluid supply connector 356.

Alternatively, the fluid supply tube may be directly connected to the fluid supply bags (300/302), eliminating the need for the fluid supply connector 356.

The heparin supply tube 352 and saline supply tube 354 join together at the fluid tube junction 353. The fluid tube junction 353 comprises a heparin input, a saline input and a combined output which extends toward the sample tube junction 320. The heparin input to the fluid tube junction 353 has a check-valve 351 which isolates the heparin tube 352 from pressure variation in the saline tube 354. The isolation provided by the check-valve 351 reduces heparin carryover or leakage during the saline flush by minimizing upstream compliance.

Figure 19:
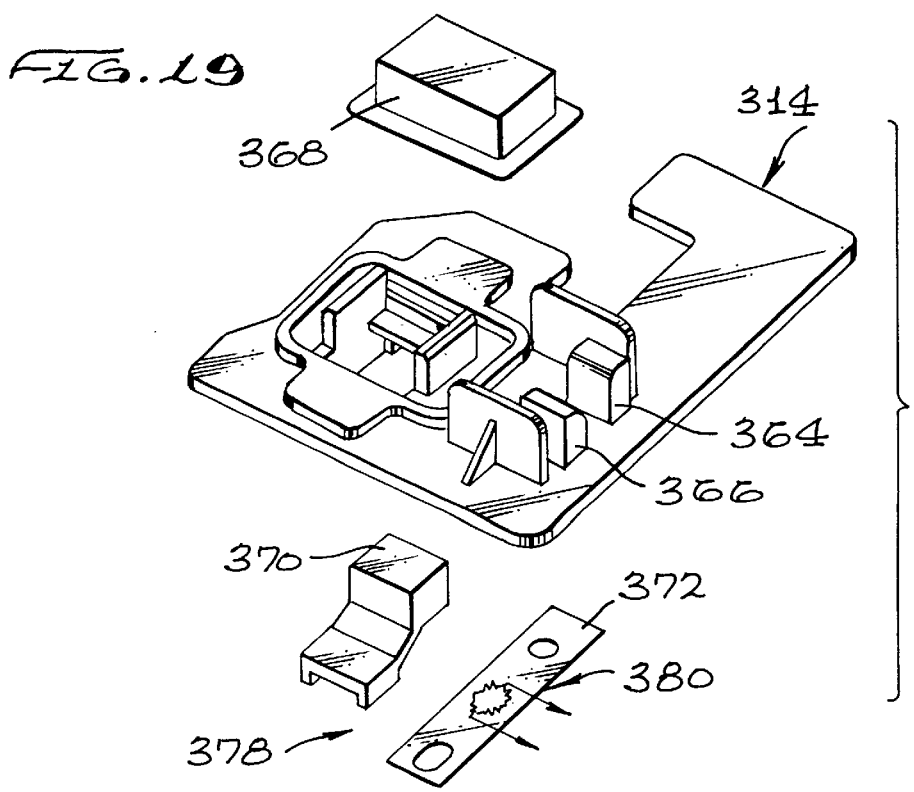
FIG. 19 shows a pressure sensing mechanism within the clamp housing holder.

The sample tube 318 connects to the fluid supply tube 306 at the sample tube junction 320. The sample tube 318 is made from a soft PVC material allowing for better interaction with the peristaltic pump 324 and for improved pressure readings, which will be described in more detail later. Referring to FIGS. 16 and 19, the sample tube 318 also has a clamp housing 316 which provides support for the slide clamp 344. The slide clamp 344 is engaged by a mechanism on the analyzer 312 for opening and closing the sample tube 318. The sample tube 318 terminates with a blood dropper 328 which allows for improved delivery of individual drops of blood during the test mode. A bi-directional patient tube 322 connects the sample tube junction 320 to the catheter connector 358.

The bidirectional patient tube 322 may contain a bidirectional extension tube 362 which allows for greater flexibility and for easier maintenance of the catheter 311 in the patient. When the bidirectional extension tube 362 is used, the bidirectional tube 322 has two quick clearing Leur fittings 360. Each Leur fitting comprises a male Leur fitting and a female Leur fitting, which mate to form a fluid path. Due to the fact that the bidirectional patient tube 322 will alternately transport heparin, saline and blood, it is important that the bidirectional patient tube can quickly be cleared of a first fluid upon start of a second fluid.

Through investigation it was found that the standard Leur cleared too slowly, allowing a first fluid to contaminate and mix with a second fluid. Specifically, the standard female Leur fitting had areas where fluid stagnated. When a second fluid started to flow, these stagnation areas held a quantify of the first fluid which became pollutants that contaminated the second fluid. Such a condition is undesirable when changing from a first fluid to a second fluid.

Referring to FIG. 17, the quick-clear Leur 360 comprises a male fitting 370 and female fitting 368. The male fitting 370 has a Leur input 366 which terminates at the Leur port 372, allowing fluid to flow from the Leur port into the female Leur fitting 368. In the quick-clear Leur fitting, the male Leur fitting 370 is modified, while the female Leur fitting 368 is an industry standard Leur fitting. Thus, mating the male Leur fitting 370 with any female Leur fitting 368 will create a quick-clear Leur fitting.

The quick-clear Leur 360 addresses the above discussed contamination problem by creating a flow pattern at the Leur port 372 which more quickly clears the first fluid from the stagnation area 364. Three configurations have been identified which more quickly clear the stagnation area 364. FIG. 17A shows the Leur input 366 concentrically placed in the male fitting 370, but the Leur port 372 has a non-circular shape. Fluid flows through the Leur input 366 and exits the Leur port 372, such that a fluid flow pattern is created whereby the second fluid more quickly clears the first fluid from the stagnation area 364.

FIG. 17B shows an alternative to a non-circular Leur port 372 by having the Leur input 366 terminate off-axis from the female fitting 368. Just as in the device of FIG. 17A, the fluid exits Leur port end 372 and creates a fluid-flow pattern that more quickly clears the stagnation area 364.

FIG. 17C shows another alternative for the fast clearing Leur 360. Here the Leur input 366 is angled such that it approaches the female fitting Leur 368 off axis relative to the centerline of the female fitting. The angling of the Leur input 366 causes the fluid flowing through the Leur input 366 to more quickly clear the first solution from the stagnation area 364.

The bidirectional extension tube 362, if present, ends in a catheter connector 358 which allows the sample/supply set 308 to connect to a catheter 311 which has been inserted into a patient's 310 vein.

Figure 18:
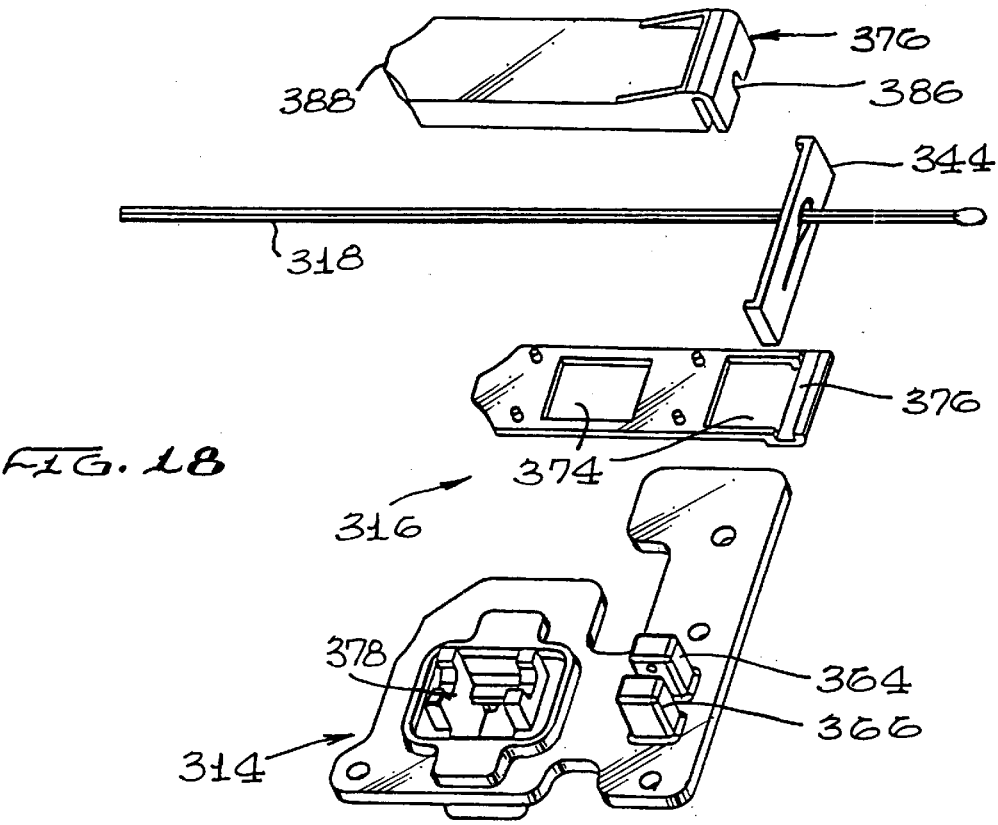
FIG. 18 shows a clamp housing and slide clamp with a sample tube.

Referring to FIG. 18, the clamp housing 316 is positioned on the sample tube 318. The clamp housing 316 comprises two mating pieces that surround the sample tube 318 to accurately position the sample tube 318 relative to the clamp housing holder 314. Additionally, the two mating pieces meet to form a clamp track 376 wherein a slide clamp 344 traverses in the clamp track 376. One of the mating pieces has openings 374 which allow the sample tube 318 to be accurately positioned between the LED 364 and the optical detector 366. Another housing opening 374 permits positioning of the sample tube 318 accurately relative to the pressure sensor mechanism 378.

FIG. 19 shows the pressure sensor mechanism 378 in more detail. The pressure sensor mechanism 378 comprises a strain gauge 372 which has strain gauge electronics 380 that measures the deflection of the strain gauge 372. The use of a strain gauge is well known in the art. The strain gauge 372 is connected to a pressure foot 370. The pressure foot 370 is placed within the clamp housing holder 314 and may be covered by a pressure membrane 368 to assure fluids and other debris do not interfere with the operation of the strain gauge 372. The pressure membrane 368 is made of material that minimally interferes with the pressure foot 370.

In operation the clamp housing 316 positions the sample tube 318 such that the sample tube 318 is positioned under compression on the pressure foot 370. Since the sample tube 318 is made of a soft material, any pressure change in the sample tube 318 will cause a slight fluctuation in the position of the pressure foot 370. This fluctuation causes a deformation of the strain gauge and changes the electronic measurement from the strain gauge electronic 380. The measurement can then be related to the fluid pressure present in the sample tube 318. The clamp housing 316 is held securely in the clamp housing holder 314 with a clamp arm which will be described later.

Figure 20:
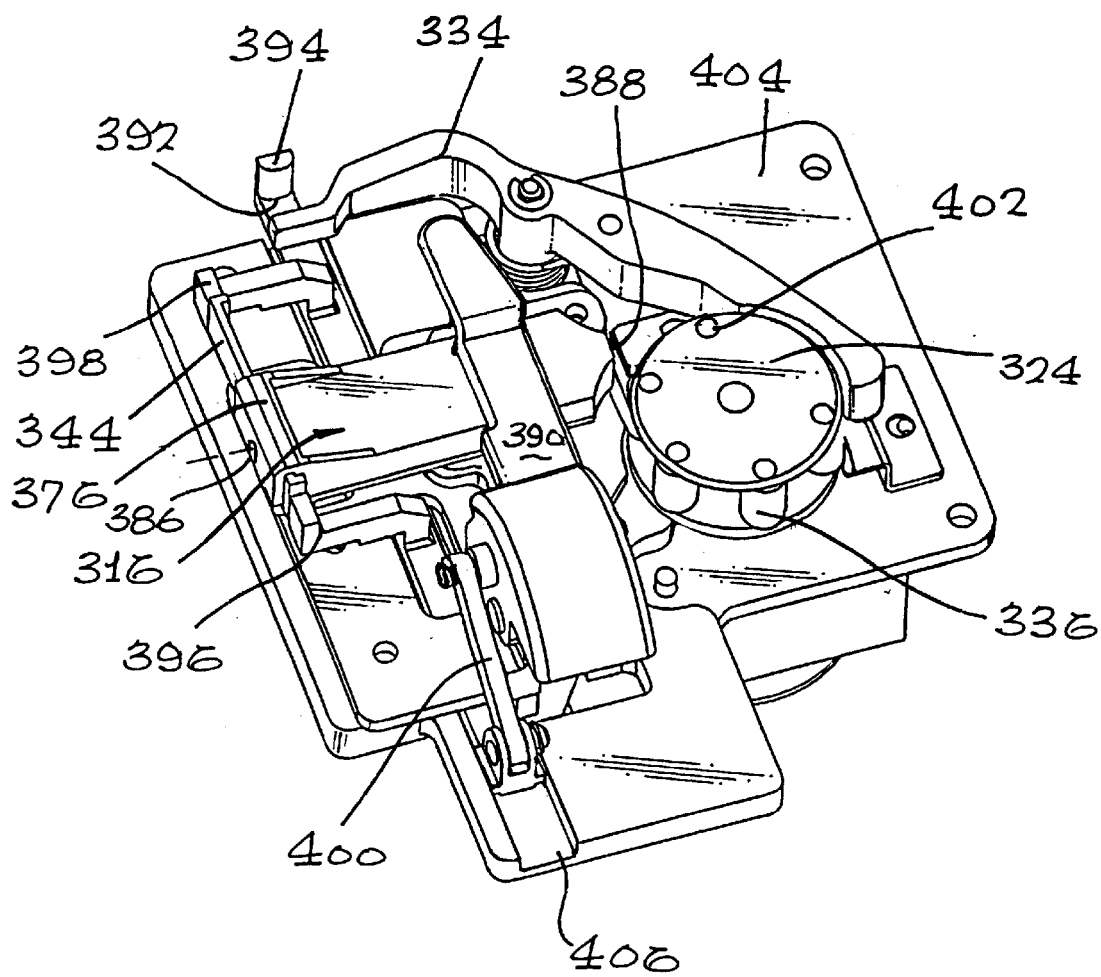
FIG. 20 shows a perspective view of an interlock system including a platen arm and roller pump.
Figure 21:
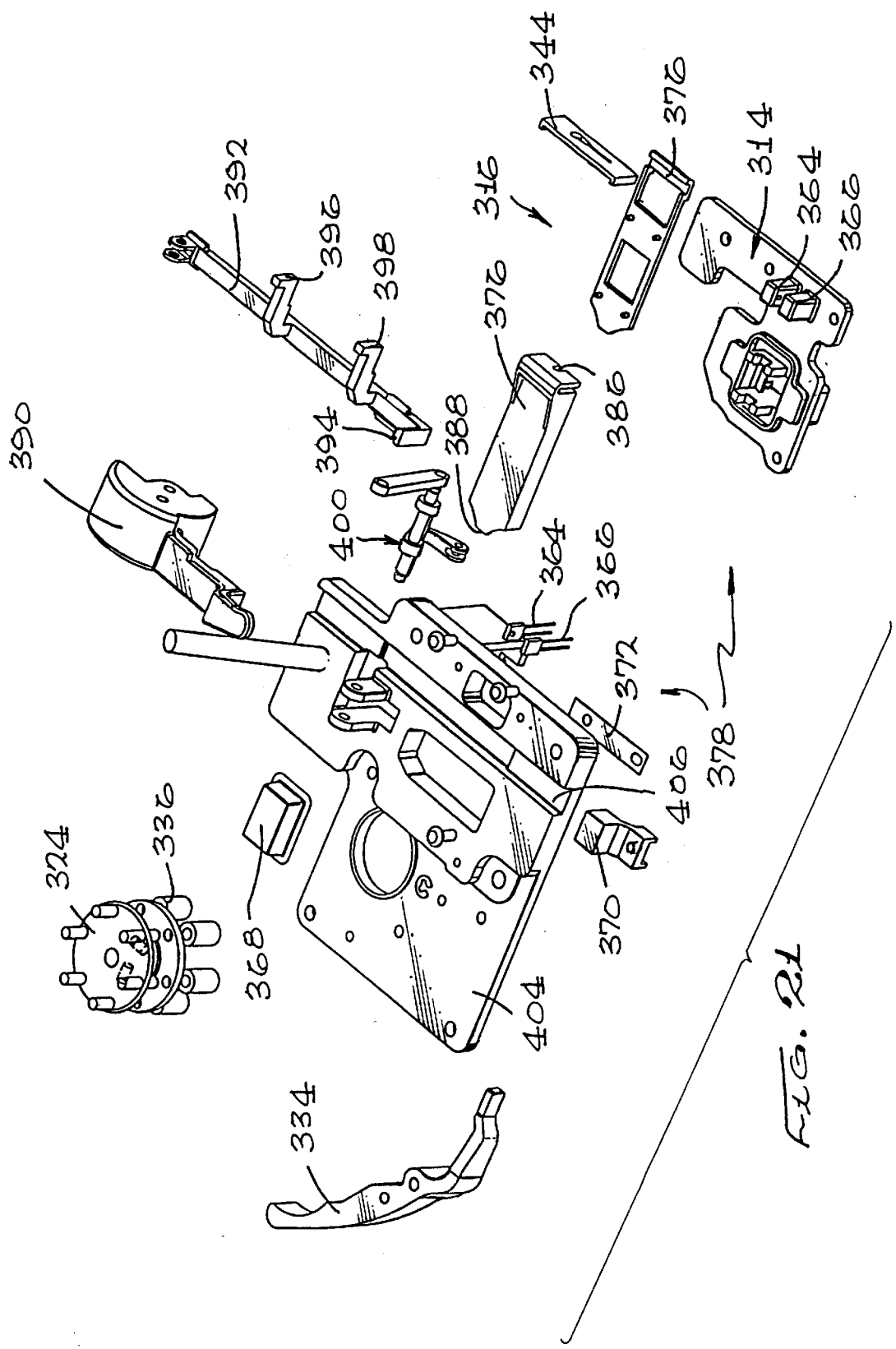
FIG. 21 shows an exploded view of an interlock system, including a clamp arm and roller pump.

FIGS. 20 and 21 show the interlock of the preferred embodiment. FIG. 20 is a perspective view of the interlock system whereas the FIG. 21 is an exploded view, showing better the individual elements of the interlock. The interlock of the preferred embodiment assures that the sample line 318 remains occluded until the peristaltic pump 324 is able to control fluid flow within the sample tube 318.

The interlock comprises a clamp arm 390 which pivots vertically relative to the interlock base 404 and connects to a push bar 392 through a arm/bar link 400. As the clamp arm 390 is rotated from an open position to a closed position, the arm/bar link 400 causes the push bar 392 to traverse in the push bar track 406. Further, the clamp arm 390 in its closed position secures the clamp housing 316 into the clamp housing holder 314.

In operation the clamp arm 390 is rotated to its open position which gives an operator access to the clamp housing holder 314. The operator places the clamp housing 316 into the clamp housing holder 314. The clamp housing 316 is positioned such that the slide clamp 344 is positioned between the clamp push tab 396 and the clamp pull tab 398. The slide clamp 344 is fully engaged, occluding the sample tube 318. Further, when the clamp arm 390 is in its open position, the push bar 392 is positioned such that the platen tab 394 engages the platen arm 334, causing the platen arm 334 to pivot away from the peristaltic pump 324. As the operator positions the clamp housing into the clamp housing holder 314, the operator places the sample tube 318 into the sample tube path 402. The sample tube path 402 extends from the tube entrance 386 through the clamp housing 316, through the tube exit 388, and between the platen 334 and peristaltic pump 324.

With the clamp housing 316 and the sample tube 318 properly in place, the operator begins to lower the clamp arm 390. As the clamp arm 390 is rotated to a lower position, the push bar 392 traverses in the push bar track such that the platen tab 394 disengages the platen arm 334, allowing the platen arm 334 to be tightly compressed against the peristaltic pump 324. At this point of this clamp arm rotation, the sample tube 318 is occluded by both the slide clamp 344 and the platen arm 334. Therefore, no fluid is allowed to flow through the sample tube 318. As the operator continues rotating the clamp arm 390 to a lower position, the push bar 392 continues to traverse in the push bar track 406 until the clamp push tab 396 engages the slide clamp 344. The slide clamp, which until this point has been in a closed position, is now pushed into an open position. The operator continues rotating the clamp 390 until the slide clamp arm comes to rest on top of the clamp housing 316, thereby securely positioning the clamp housing 316 into the clamp housing holder 314.

When the operator desires to remove the clamp housing 316 from the clamp housing holder 314, the progression is reversed. First, the operator begins rotating the clamp arm 390 upwardly. This removes the tension from the clamp housing 316. As the clamp arm 390 is rotated upward the clamp pull tab 398 contacts the slide clamp 344 and pushes the slide clamp 344 into a locked position where the sample tube 318 is occluded. As the operator continues to rotate the clamp arm 390 upward the platen tab 394 engages the platen arm 334 and rotates the platen arm 334 away from the peristaltic pump 324, thus allowing the sample tube 318 to be removed from between the platen arm 334 and the peristaltic pump 324. With the clamp arm 390 raised, the clamp housing 316 maybe removed from the clamp housing holder 314.

With the interlock detailed, additional information is now provided on the structure used to select and move slide 346 into the test area 330. As shown in FIG. 22, each slide contains a tab engagement hole 436 which is an indentation or hole placed near the corner of the slide 346. Referring now to FIG. 23, several of these slides 346 may be vertically stacked in a slide cassette 332. In the preferred embodiment the slide cassette 332 holds up to 6 slides 346 in a vertical arrangement. Those skilled in the art will recognize that different numbers and arrangements of slides are readily available. The slide cassette 332 is an independent unit which is placed by an operator into the cassette tray 414.

The cassette tray 414 may be adjusted vertically relative to the test area 330. A vertical stepper motor 420 rotates a vertical screw 416 which is connected to the cassette tray 414. As the vertical stepper motor 420 rotates, the vertical screw 416 causes the cassette tray 414 to rise or lower depending upon the direction of rotation of the vertical stepper motor 420. A vertical guide 418 assists in keeping the cassette tray 414 aligned and in proper position.

Once the slide cassette 332 is in the proper vertical position, a horizontal stepper motor 422 pushes an individual slide 346 from the slide cassette 332. The horizontal stepper motor 422 has a screw which connects to the horizontal screw nut 428 (referring to FIG. 24). The horizontal screw nut 428 connects to a horizontal track 424 via a horizontal track guide 426, which assists in keeping the horizontal screw nut 428 properly aligned. As the horizontal stepper motor 422 is rotated, the horizontal screw nut 428 is either pushed or pulled relative to the slide cassette 332. As the horizontal stepper motor 422 pushes the horizontal screw nut 428 outward, the horizontal push area 430 contacts a corner of the slide 346, pushing the slide 346 from the slide cassette 332. The horizontal stepper motor 422 continues pushing the slide 346 from the slide cassette 332 until the slide is properly positioned over the test area 330.

The test area 330 has an optical source and sensor which communicate with the capillary channel 351 on the slide to detect if a physical change has occurred on the slide due to the presence of a target substance in the blood. When the test is complete and the slide is to be retracted into the slide cassette 332, the horizontal stepper motor reverses direction. The horizontal screw nut 428 has a slide tab 432 having a slide hook 434. The slide hook 434 engages the tab engagement hole 436 on the slide 346 as the slide hook 434 is pulled back by the horizontal screw nut 428.

The horizontal stepper motor 422, in conjunction with the horizontal screw nut 428 and the slide hook 434, pulls the slide 346 back into the slide cassette 332 until the slide 346 is in its original position. At this point the horizontal stepper motor 422 stops. The vertical stepper motor 420 now engages and lowers the slide cassette 332 sufficiently to allow the slide hook 434 to disengage the tab engagement hole 436. Once disengaged, the vertical stepper motor 420 stops and the horizontal stepper motor 422 once again engages to pull the horizontal screw nut 428 to an at-rest position where it is out of the way of the slide cassette 332.

Figure 25:
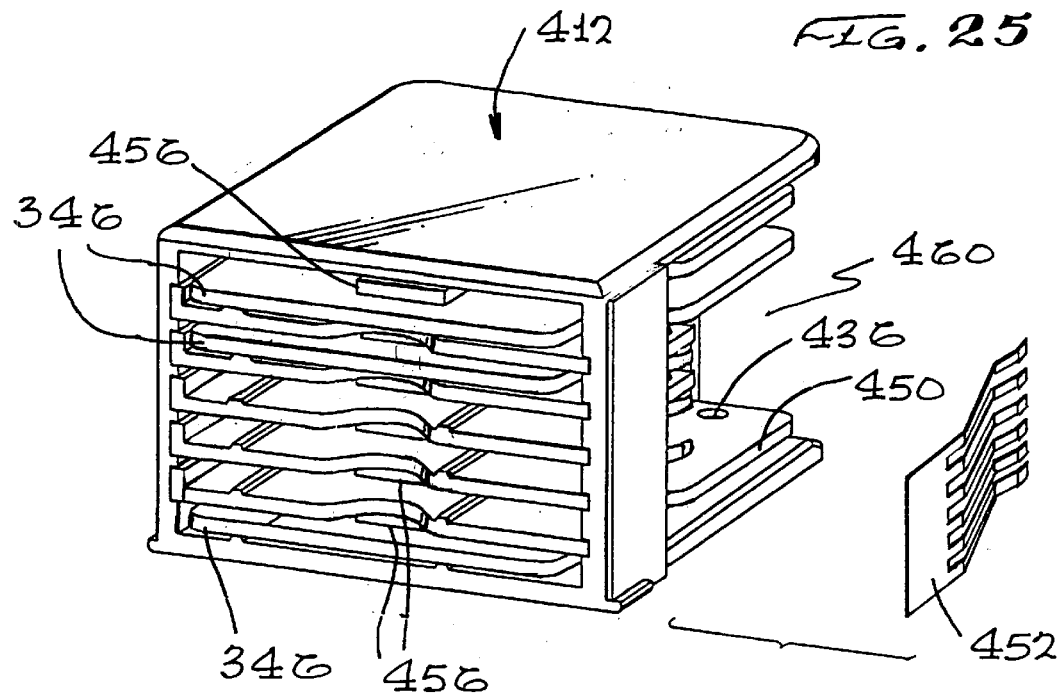
FIG. 25 shows a stacked reagent cassette.

FIG. 25 details the slide cassette 332. In the preferred embodiment the slide cassette 332 holds up to six slides 346 in a vertical stacked configuration. FIG. 25 shows three slides 346 positioned in the slide cassette 332. The slide cassette 332 has an open side 460 which allows access to the engagement hole 436 of the slide 346. Optionally, a spring clip 452 may be attached to the open side which engages a spring clip engagement tab 450 on the slide 346 to assist in holding the slides 346 in place.

The reagents present on the slide are often sensitive to atmospheric conditions. In particular, reagents typically have a short-shelf life after being removed from their sealed container. For example, once a slide is removed from its sealed container and is allowed to contact air, humidity from the air may degradate the reagent and cause it not to react properly. On the slide 346, air may enter the capillary channel 351 from the vent hole 411 or the blood dropper area 349. With air reaching the reagent in the capillary channel 351, an opened slide has a limited useful life. To increase the useful life of the slides 346, the preferred embodiment places a closed-cell foam gasket 456 on the shelf bottom surface 454 above each slide 346.

Figure 26:
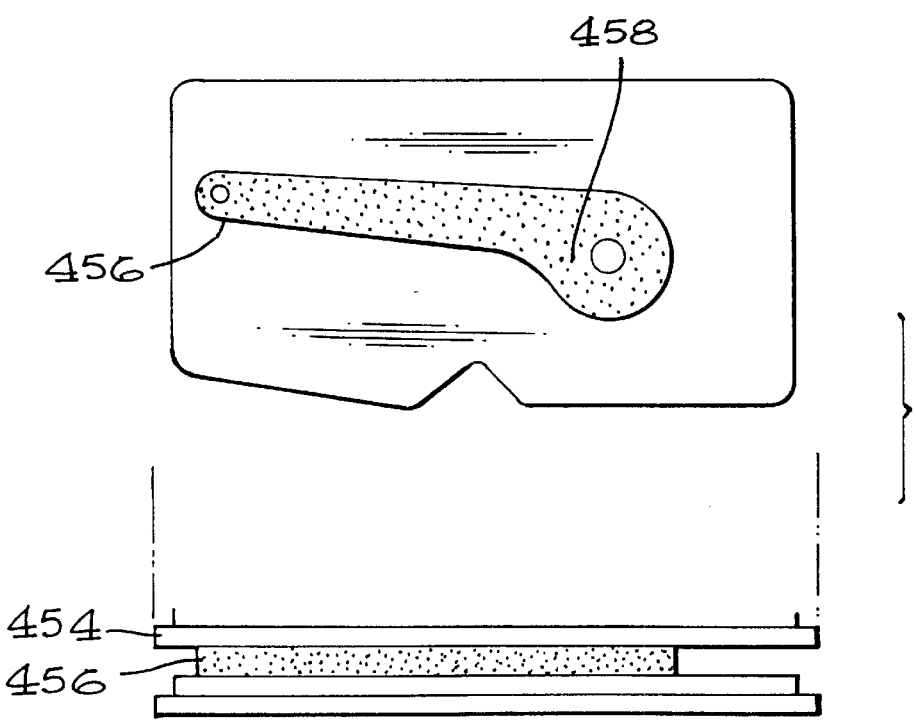
FIG. 26 shows a foam gasket used to protect the reagent on a reagent slide inserted into the slide cassette.

Referring to FIG. 26, the foam gasket is sized and positioned such that the blood dropper area 349 and the vent hole 411 are sealed by the foam gasket 456. The closedcell foam gasket presses against the slide 346 to provide a tortuous path for humid air to reach the reagent. By sealing the capillary channel 351, the useful life of an opened slide is extended. The foam is in a tear-drop shape such that the narrower end of the tear-drop shape ends up near a corner of a slide 346. Through experimentation this shape was found to be most effective by 1) providing protection to the reagent and 2) minimizing the spreading of blood when the slide was retracted into the slide cassette 332 after testing. Those skilled in the art will readily recognize other alternative shapes for the foam gasket 456.

Moving now to the blood dropper mechanism, the blood dropper mechanism comprises a stepper motor driving a screw that causes a blood dropper head to traverse laterally on a blood dropper arm. The sample tube 318 terminates in a blood dropper that is received into the blood dropper head.

The dropper head may be positioned in an out-of-the way standby area. As a flushing cycle initiates, the stepper motor activates to move the blood dropper head from the standby area to the waste container. The waste container has a spring loaded cover over the waste opening, and the waste cover has a dropper arm tab which is engaged by the blood dropper head as the dropper head moves over the waste container. Therefore, when the blood dropper head is positioned in the standby area, the waste container opening is tensioned closed, but as the blood dropper head is moved over the waste container the blood dropper head engages the blood dropper tab on the opening cover and opens the cover to the waste container. With the blood dropper 328 positioned above the now open waste container, the peristaltic pump may start and any liquid pumped through the sample tube 318 will be pushed from the blood dropper 328 and will fall into the waste container.

At the start of the test cycle, the stepper motor moves the blood dropper head to the test area 330. As described previously, a slide 346 is positioned into the test area 330 such that the blood dropper area 349 of the test slide 346 is located above the test area 330. The peristaltic 324 pump is now activated for a short time, thereby pushing one or more drops of blood out of the blood dropper 325, which fall onto the blood dropper area 349 of the slide 346. After the blood has been deposited on the slide 346, the blood dropper head is moved back to its position above the waste container to await a flush cycle.

As discussed above, the preferred embodiment analyzes a blood sample to measure the effect of heparin on the blood sample's ability to clot. In the preferred embodiment, the test performed specifically identifies the time it takes for blood to clot when contacting a particular reagent using an optical test sensor system. The faster the blood clots, the less effect the patient is receiving from the heparin present in the patient's blood sample and conversely, the longer the blood flows, the more heparin that is present in the blood. By accurately determining how long it takes for the blood to stop flowing, the effect of the heparin in the blood system can be calculated. In the preferred embodiment, the optical test sensor is a coagulation tester that is purchased as a unit. Those skilled in the art will recognize OEM coagulation testers are readily available. The coagulation tester has a slot where a slide 346 may be inserted. Once the slide 346 is inserted, a laser light is shown through the capillary channel 351 and detected by a light detector. When the slide is placed in the coagulation tester and blood is placed on the blood dropper area 349, the blood flows to the reagent through the capillary channel 35 1. The laser and a detector detect the first flow of blood in the capillary channel 351. The system captures this time as $T_0$. As the blood continues to flow through the capillary channel 35 1, the blood continues coagulating as it contacts the reagent. Once sufficient blood has coagulated to stop the flow of blood in the capillary channel 351, the light no longer detects fluid motion. The system measures this time as $T_1$. By calculating the elapsed time between $T_0$ and $T_1$, the system determines a length of time that the blood sample took to reach a known stage of coagulation ($\Delta T$). The coagulation tester relates the $\Delta T$ to the effect of the heparin in the blood system. This measured effect is sent via an RS232 communication interface to the controller 336. Based on the measured heparin effect and the desired heparin effect as set by an operator, the controller determines a new rate of heparin infusion.

During the next infusion cycle, the pump 304 will infuse at the new rate.

The controller 336 will now be discussed. The preferred embodiment contains a controller that controls various aspects of the feedback control drug system. The controller's activity can be divided into three broad categories: (1) background activity, (2) blood sample drawing procedure, and (3) heparin fluid delivery procedure.

Background activity includes all controller activities not directed to the delivery of the heparin or of the sampling of blood. This background activity includes a periodic self test wherein the controller interrogates various components of the preferred embodiment to assure the system is performing properly. For example, the controller interrogates the IV pump to assure the IV pump is infusing heparin at the proper rate and to assure the IV pump is in proper working condition. If a self-test fails, then the controller activates an audio or visual alarm or other means to notify an operator that the system is not working properly.

Further, the preferred embodiment has a user interface whereby an operator may input commands to the system and also receives information from the preferred embodiment via an electronic display. In background mode, the controller is responsible for updating the display with information such as current time, current flow rates, and the time until next blood sampling. Of course, those skilled in the art will recognize that various types of displays and information may be used to communicate to an operator.

The controller is also responsible for monitoring the input to the user interface which is generally a key pad. Through the keys the user can input patient specific information and control the operation of the system.

Alternatively, input may be received via bar code readers, external key pads, or even from an electronic source. Those skilled in the art will recognize several available means to communicate commands to the preferred embodiment. When an operator interacts with the input controls of the preferred embodiment, the controller handles the interruption and makes an appropriate adjustment to the preferred embodiments operation. For example, if an operator approaches the key pad and instructs through the user interface that the preferred embodiment should immediately draw a new sample of blood and analyze that blood for its heparin effect, the controller will deactivate the heparin delivery system and begin the blood drawing procedure. There are additional color indicator lights that show the basic operational state of the system. An audio device is incorporated to draw user attention to the system during alerts and alarms. An infrared printer interface is provided in order to create a permanent record of the heparin therapy, if desired.

When directed by the controller or operator, the controller may leave the background procedure and initiate the drawing procedure. A drawing procedure is activated by either manual intervention by an operator or when a preset time has arrived. The preset time is determined by the heparin procedure which will be discussed in a later section.

With the background procedure detailed, the discussion now moves to the drawing procedure. The drawing procedure is used to prepare the preferred embodiment to accept a sample of blood from the patient, to draw the sample of blood from the patient, to deliver the blood sample for analysis, and to return the preferred embodiment to a state for continuing heparin infusion. The drawing procedure is divided into four distinct cycles: (1) calibration cycle; (2) sample cycle; (3) flush cycle; and the (4) abort cycle. Each of these cycles is discussed below.

At least once before starting to draw a sample, a calibration cycle is initiated. In the calibration cycle, the controller first interrogates the strain gauge to assure the sample tube 318 is properly placed relative to the beam and that the power is on. Next the controller establishes communication with the IV pump to terminate heparin delivery and begin a saline solution flush to clear the fluid supply 306 and sample tube 318 as described earlier. In clearing the sample tube 318, the controller additionally controls the peristaltic pump to allow fluid to flow through the sample tube 318 and into the waste container 338. Once the flush is complete, the controller takes strain gauge readings over a period of time and determines a static base line pressure value. Once the controller is assured the strain gauge is functioning properly, the controller signals to start the sample cycle.

The sample cycle begins by activating a start draw function. The start draw function activates the peristaltic pump 324 to start drawing a sample at a predetermined rate. This rate is increased in predetermined steps until a maximum sample rate is reached. Once the maximum sample rate is reached, the sample cycle changes to a monitor function.

The monitor function may also be activated if the controller detects certain conditions during the start draw function. These conditions include a no-flow condition which would be indicated by an decreased pressure reading and a low estimated volume flowing in the sample tube, or by a condition where pressure sensed by the strain gauge is lower than a base line value. Once the monitor function is activated, either by the achievement of maximum flow rate or because a no-flow or low pressure reading was detected, the monitor function increases the sample pump rate by a predetermined amount until the maximum sample rate has been achieved. However, if the strain gauge pressure reading is still below a base line value, the sample pump rate is reduced.

Further, if a no-flow condition is determined to exist, the preferred embodiment will attempt to mitigate the no-flow condition. The preferred embodiment includes a pressure cuff to assist in the drawing function, so in a no-flow condition the preferred embodiment will attempt to mitigate by deflating and then reinflating the cuff and reattempting the draw. If the no flow condition still exists, then the pressure cuff will be increased even more and then a draw attempted again. Further, the peristaltic pump may momentarily reverse directions to force fluid to flow back into the patient's vein, thereby clearing an obstruction in the catheter or reopening a collapsed vein. Those skilled in the art will recognize other means for correcting a no-flow condition while drawing blood.

During the monitor function, the controller also calculates the volume of blood drawn from the patient. Further, if the preferred embodiment includes an optical sensor in the clamp housing 314, the controller will also monitor for when the leading edge of the blood sample enters the clamp housing holder 314. Once the controller determines that blood is flowing through the blood dropper 328, the peristaltic pump is stopped, the dropper arm 340 positions the blood dropper over the test area 330 and the peristaltic pump is momentarily started to deposit a drop or two of blood onto the slide 346.

Once the blood has been placed on the slide 346, the system activates the flush cycle which has already been discussed above. The flush cycle can alternatively be activated when an abort signal is received.

The abort signal may be received because the controller detects an error condition within the preferred embodiment or an operator manually initiates an abort cycle.

The last major function of the controller is to control the heparin delivery procedure. The heparin fluid delivery procedure is used to (1) determine the rate for heparin delivery during the background procedure, and (2) determine the next time the preferred embodiment will take and analyze a blood sample. The preferred embodiment is used to achieve and maintain a target level for the effect of the heparin in a patient's blood. This target effect may be determined by medical personnel, and is input into the preferred embodiment via the user interface. Further, medical personnel may input patient-specific information such as age, weight, sex, whether or not this patient is a smoker, and other drugs the patient may be on. If sufficient patient-specific information is input into the system, the system may assist in determining the target effect.

Once the patient is connected to the preferred embodiment, the necessary patient information has been entered, and all fluid lines are connected, the operator can "start" the closed loop drug delivery system. The system will acquire and analyze a blood sample to determine the patient's initial coagulation time. This initial time to coagulate is compared to the patient specific information, and if an inconsistency is found, the operator is notified and the system does not proceed to infuse heparin. For example, if it is input that the patient has already received heparin from another source, the initial sample analysis should indicate a correspondingly long coagulation time. If the initial reading is not consistent with the patient having received a bolus of heparin, the operator is notified as discussed above.

If the initial coagulation time is consistent with having received a previous bolus of heparin, the preferred embodiment begins to infuse heparin in an open-loop condition. The amount of heparin infused is calculated by the preferred embodiment to gradually allow coagulation time to decrease to the target effect. Periodically during open-loop infusion the system will draw and test a blood sample to determine if the heparin effect is decreasing. Once the heparin effect is seen to be decreasing (coagulation time is increasing), then the system will begin infusing in a closed-loop manner to reach and maintain the target effect.

If the patient has received no heparin infusion before connection to the preferred embodiment, and an initial sample and analysis is consistent with this input, the system will assume the patient to be at a base line time level for coagulation. With a base line established, the controller now calculates an optimal infusion rate to achieve the target effect.

As discussed above, the preferred embodiment analyzes a blood sample to get a measurement of the effect of heparin in the patient's blood. Based on this measurement and the target effect, the system will command the infusion pump to deliver heparin at a rate that will optimally achieve the target effect. However, this optimal rate may be adjusted by data received from the infusion pump or by an operator input.

During infusion, the infusion pump is communicating infusion data to the controller. For example, the infusion pump may notify the controller that a reduced amount or no heparin was infused for a period of time. Such a lapse in infusion rate could be caused by the heparin bag being changed or a temporarily obstructed fluid tube, for example. After normal infusion is resumed, the preferred embodiment will increase heparin delivery above the optimum rate to compensate for the period of reduced or no infusion. Thus, heparin delivery rate is periodically adjusted due to inputs from the infusion pump.

Further, the operator has the flexibility to change the target heparin effect, initiate a sample procedure or override the system. Thus, the preferred embodiment will adjust the current rate of heparin to accommodate new instructions from an operator. For example, the operator may desire a temporary increase or decrease in infusion rate, so the system will correspondingly respond with an adjusted rate of infusion.

Another primary task of the heparin fluid delivery procedure is to calculate a time-optimal infusion profile to achieve the desired anticoagulant state of the patient in a safe manner, based on previous measurements. This conserves patient blood sampling and thus the number and frequency of measurements.

The feedback-controlled delivery of heparin can be achieved based on sparse level measurements, therefore measurements need not be obtained frequently. Typically, samples need be taken only every few hours. The infusion rate calculated by the heparin control algorithm is based on a pharmacodynamic (PD) model of heparin response. Since patient variability in response is large, there are a number of parameters in the PD model that describe the individual's response. Based on measurements of patient response the model parameters can be adjusted (using for example, Bayesian estimation). Since the measurements are sparse and subject to some error, the patient parameter estimates will have a certain confidence interval which will affect the expected control accuracy.

A potential advantage of computerized feedback-controlled drug delivery with sparse measurements is the ability to optimize the sampling schedule. Although the system itself poses some limitations on the frequency of measurements (cost, limited number of cartridges), the control algorithm can determine when the additional information from a new measurement would be most beneficial based on the observed patient response, the history of infusion adjustment, the desired accuracy of control, and the confidence in the model parameters.

Although the preferred embodiment discussed above specifically addresses a heparin infusion system, the invention encompasses other closed-loop drug delivery systems. For example, another preferred embodiment comprises the feedback controlled drug delivery system infusing glucose and/or insulin therapeutic fluid based on the concentration of glucose present in a blood sample. In this embodiment a patient, possibly diabetic, is connected to the feedback controlled drug delivery system. An operator inputs patient specific information, including a target glucose level, and starts the system. An initial blood sample is taken and analyzed for a glucose level. Based on the initial and target levels, the preferred embodiment infuses glucose and/or insulin to achieve the target level.

While embodiments and applications of his invention have been shown and described, it would be apparent to those in the field that many more modifications are possible without departing from the inventive concepts herein. The invention, therefore, is not to be restricted except in the spirit of the appended claims.

We claim:

1. An apparatus for delivering a therapeutic solution to a patient at an intravenous entry point during a first time period and removing a patient fluid sample from the intravenous entry point during a second time period for analysis, the apparatus comprising:
   a fluid supply tube connected to the therapeutic solution;
   a sample tube junction connected to the fluid supply tube;
   a bi-directional patient tube having a fluid flow and extending from the sample tube junction to the intravenous entry point, whereby the fluid flow is toward the intravenous entry point during the first time period and away from the intravenous entry point during the second time period;
   a sample tube connected to the sample tube junction; and
   a housing positioned on the sample tube, wherein the housing further comprises a pressure junction adjacent to the sample tube.

2. The apparatus claim 1 wherein said fluid supply tube comprises a check-valve.

3. The apparatus of claim 1 wherein said apparatus is disposable after a single use.

4. The apparatus of claim 1, wherein the housing includes a detection window to detect the presence of blood in the fluid path.

5. The apparatus of claim 1 where the sample tube and the fluid supply tube are of different materials.

6. The apparatus of claim 1 further comprising a pump, wherein the pump engages the sample tube.

7. The apparatus of claim 1 further comprising a slide clamp operably engaging the sample tube.

8. The apparatus of claim 1 further comprising a flushing tube connecting a flushing fluid to the fluid supply tube.

9. The apparatus of claim 1 further comprising a pressure sensor and a keyed housing holder for receiving the housing wherein placing the housing in the keyed housing holder positions the pressure junction against the pressure sensor.

10. The apparatus of claim 1 wherein the bi-directional patient tube comprises at least two connected tubes.

11. The apparatus of claim 1, further comprising an analyzer coupled to the sample tube and configured to receive fluid from the sample tube.

12. The apparatus of claim 11, wherein said analyzer comprises a reagent cassette providing environmental control for a plurality of reagent slides, each reagent slide having a port that allows air to contact a degradable reagent, the reagent cassette comprising:
   a cassette housing having a top and a plurality of shelves, each shelf and top having a bottom surface wherein each reagent slide in the reagent cassette is positioned on a shelf and adjacent to a bottom surface;
   a closed-cell foam gasket positioned on each bottom surface wherein the closed cell foam gasket is positioned surrounding the port and compressed against the reagent slide when the slide is loaded in the reagent cassette.

13. The apparatus of claim 12, where said cassette housing is keyed to align with a reagent cassette holder.

14. The apparatus of claim 11, further comprising an interlocking apparatus for a fluid tube connecting a patient to the analyzer, the interlocking apparatus comprising:
   a clamp housing on the fluid tube having a slide clamp engaging the fluid tube;
   a roller pump having at least one roller;
   a platen arm collapsing the fluid tube against the roller;
   a clamp arm holding the clamp housing into the housing holder and operatively connected to the slide clamp; and
   a bar operably connecting the clamp arm to the platen arm, wherein the slide clamp is only opened after the platen has collapsed the fluid tube against the roller and the slide clamp is closed before releasing the platen from against the roller.

15. The apparatus of claim 12, further comprising an interlocking apparatus for said sample tube, said interlocking apparatus comprising a slide clamp on the sample tube; a platen arm positioned adjacent to rollers of a roller pump, wherein the sample tube is interposed between the platen arm and the rollers; a bar operably engaging the slide clamp and the platen arm, whereby the bar positions the platen arm away from the roller pump, thereby opening and releasing the sample tube, and alternatively, positions the platen arm toward the roller pump, thereby pressing the platen arm against the roller pump and occluding the sample tube;
   wherein the bar has at least a first, second, and third position such that in the first position the platen arm is away from the roller pump and the slide clamp is closed; in the second position the platen arm is pressed against the roller pump and the slide clamp is closed; and in the third position the platen arm is pressed against the roller pump and the slide clamp is open, and the interlocking apparatus follows the sequence of first to second to third position, and alternatively, follows the sequence of third to second to first position.

16. The apparatus of claim 12, further comprising a drawing pressure source operably connected to the sample line for creating a drawing pressure in the sample line, the drawing pressure being controlled by a controller;
   wherein the controller directs the drawing pressure to draw the patient sample to the analyzer, directs the analyzer to perform the measurement, receives the measurement, and directs the fluid source to deliver the therapeutic solution at a rate based on the measurement.

17. The apparatus of claim 1, further comprising a Leur connector set having a male Leur fitting and a female Leur fitting and the male Leur fitting having a Leur input that terminates in a Leur port, wherein the Leur includes a non-circular terminus.

18. The apparatus of claim 1, further comprising a male Leur fitting and a female Leur fitting with the male Leur fitting having a Leur input that terminates in a Leur port, wherein the Leur port is disposed non-concentrically in the female Leur fitting.

19. The apparatus of claim 1, further comprising a male Leur fitting and a female Leur fitting with the male Leur fitting having a Leur input that terminates in a Leur port, the improvement comprising a Leur connector set having a male Leur fitting a female Leur fitting with the male Leur fitting having a Leur input that terminates in a Leur port, wherein the Leur input lumen is placed off axis from the centerline of the male Leur.

20. A device for the feedback controlled delivery of a therapeutic fluid to a patient, comprising:
   a catheter invasively attached to the patient and connected to a fluid supply tube;
   a therapeutic fluid source connected to the fluid supply tube and delivering the therapeutic fluid to the patient as directed by a controller;
   an analyzer for measuring the therapeutic solution in a patient sample, and communicating the results of the measurement to the controller;
   a sample tube connecting the analyzer to the fluid supply tube;
   a drawing pressure source operably connected to the sample line for creating a drawing pressure in the sample line, the drawing pressure being controlled by a controller;
   wherein the controller directs the drawing pressure to draw the patient sample to the analyzer, directs the analyzer to perform the measurement, receives the measurement, and directs the fluid source to deliver the therapeutic solution at a rate based on the measurement.

21. The device of claim 20, further comprising a flushing fluid source connected to the fluid supply tube and under the control of the controller.

22. The device of claim 20, wherein the therapeutic fluid is heparin and the patient sample is blood.

23. The device of claim 22, wherein the analyzer measurement measures the effect of the heparin in the blood.

24. The device of claim 20, wherein the therapeutic fluid is glucose.

25. The device of claim 20, wherein the therapeutic fluid is insulin.

26. The device of claim 20, further comprising a second therapeutic solution connected to the fluid supply.

27. The device of claim 26, wherein the therapeutic solution is glucose and the second therapeutic solution is insulin.

28. The device of claim 20, wherein the patent sample is blood and the measurement is the time it takes for a blood sample to clot.

29. The device of claim 20, wherein the measurement is the level of glucose in the patient sample.

* * * * *